United States Patent
Zhu

(10) Patent No.: US 7,145,655 B2
(45) Date of Patent: Dec. 5, 2006

(54) METHODS AND APPARATUS FOR MEASURING REFRACTIVE INDEX AND OPTICAL ABSORPTION DIFFERENCES

(75) Inventor: Xiangdong Zhu, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 11/145,155

(22) Filed: Jun. 3, 2005

(65) Prior Publication Data
US 2005/0225762 A1   Oct. 13, 2005

Related U.S. Application Data

(62) Division of application No. 10/272,357, filed on Oct. 15, 2002, now Pat. No. 6,917,428.

(60) Provisional application No. 60/329,665, filed on Oct. 15, 2001.

(51) Int. Cl.
   *G01J 4/00*   (2006.01)
(52) U.S. Cl. .................. 356/369; 356/128; 356/432
(58) Field of Classification Search .............. 356/369, 356/370, 364, 128, 432; 250/559.09, 225
See application file for complete search history.

(56) References Cited

U.S. PATENT DOCUMENTS

| | | | |
|---|---|---|---|
| 6,268,916 B1* | 7/2001 | Lee et al. | 356/369 |
| 6,734,968 B1* | 5/2004 | Wang et al. | 356/369 |
| 6,804,003 B1* | 10/2004 | Wang et al. | 356/369 |

* cited by examiner

*Primary Examiner*—Hwa (Andrew) Lee
*Assistant Examiner*—Roy M. Punnoose
(74) *Attorney, Agent, or Firm*—Fenwick & West LLP

(57) ABSTRACT

Methods and instruments are provided for measuring differences in fractional reflectivity changes between transverse electric (TE or s-polarized) and transverse magnetic (TM or p-polarized) components of an obliquely incident light with high sensitivity and low noise. Also provided are high sensitivity, low noise methods and instruments for measuring differences in fractional reflectivity changes between R-polarized (right-circularly polarized) and L-polarized (left-circularly polarized) components of a near-normal incident light. The methods take advantage of a nulling step to minimize harmonics of the optical signal derived from a first sample. Determination of odd and even harmonics of the optical signal derived from a second sample allows determination of refractive index and optical absorption coefficient differences between two samples to be determined with high sensitivity and low noise.

25 Claims, 10 Drawing Sheets

METHODS AND APPARATUS FOR MEASURING REFRACTIVE INDEX AND OPTICAL ABSORPTION DIFFERENCES

CROSS-REFERENCE TO RELATED APPLICATIONS

This application is a divisional of U.S. patent application Ser. No. 10/272,357, filed Oct. 15, 2002, now U.S. Pat. No. 6,917,428 which claims the benefit of U.S. Provisional patent application Ser. No. 60/329,665, filed Oct. 15, 2001, the entire disclosures of which are hereby incorporated by reference.

STATEMENT REGARDING FEDERALLY SPONSORED RESEARCH

Not applicable.

REFERENCE TO A MICROFICHE APPENDIX

Not applicable

BACKGROUND OF THE INVENTION

The invention relates to the field of optics and more particularly to optical ellipsometry-based methods and apparatus for measuring refractive index and optical absorption differences.

Optical ellipsometry-based methods for measuring refractive index and optical absorption of materials are known in the art and have been used to study a wide-variety of different materials. Prior art ellipsometry methods, however, tend to lack the signal-to-noise ratios necessary to detect changes in optical response from a few percent of one monoatomic or monomolecular layer, thus in general restricting their use to systems giving rise to changes greater or much greater than a few percent of one monoatomic or monomolecular layer. In cases of special forms of ellipsometry such as oblique-incidence optical reflectance difference and surface photo-absorption, prior art ellipsometry techniques teach the measurement of only one or one combination of the refractive index and the optical absorption coefficient rather than two, and so fail to realize the benefits of simultaneous determinations of refractive index and optical absorption coefficient differences. Prior art ellipsometry techniques also fail to provide a solution to the problem of determining a refractive index difference or an optical absorption coefficient difference between two samples under circumstances in which the signal-to-noise ratios of the first or the second order harmonic is inadequate because of environmental or instrument noise in these regions of the spectrum.

The present invention addresses these and other deficiencies of the prior art by providing methods and apparatus for determining refractive index and optical absorption coefficient differences with significantly improved signal-to-noise properties, for simultaneous monitoring of refractive index and optical absorption coefficient differences, and for obtaining higher order harmonic measurements.

BRIEF SUMMARY OF THE INVENTION

In one aspect, the invention provides for a method of determining a refractive index difference between two samples, the method comprising illuminating a first sample at an oblique incidence angle with a polarized incident light beam, said first sample reflecting at least some of said incident light beam to form a reflected light beam;

modulating at a modulation frequency the polarization of at least one of said incident light beam and said reflected light beam;

nulling said reflected light beam by interacting said incident light beam or said reflected light beam with a phase shifter and adjusting a phase difference between an s-polarized component and a p-polarized component of said reflected light beam, wherein said adjustment minimizes an odd modulation frequency harmonic of said reflected light beam intensity;

without further adjustment of said phase difference, illuminating a second sample at said oblique incidence angle with said incident light beam, said second sample reflecting at least some of said incident light beam to form a second reflected light beam; and determining a magnitude of an odd modulation frequency harmonic of said second reflected light beam intensity, wherein said magnitude corresponds to a refractive index difference between said first and said second samples.

In another aspect, the invention provides for a method of determining a refractive index difference between two samples, the method comprising illuminating a first sample at a near-normal incidence angle with an incident light beam, said first sample reflecting at least some of said incident light beam to form a reflected light beam;

modulating at a modulation frequency the polarization of at least one of said incident light beam and said reflected light beam;

nulling said reflected light beam by interacting said incident light beam or said reflected light beam with a phase shifter for circularly-polarized light and adjusting a phase difference between a right-circularly polarized component and a left-circularly polarized component of said reflected light beam, wherein said adjustment minimizes an odd modulation frequency harmonic of said reflected light beam intensity;

without further adjustment of said phase difference, illuminating a second sample at said near-normal incidence angle with said incident light beam, said second sample reflecting at least some of said incident light beam to form a second reflected light beam; and determining a magnitude of an odd modulation frequency harmonic of said second reflected light beam intensity, wherein said magnitude corresponds to a refractive index difference between said first and said second samples.

In yet another aspect, the invention provides for a method of determining an optical absorption coefficient difference between two samples, the method comprising illuminating a first sample at an oblique incidence angle with a polarized incident light beam, said first sample reflecting at least some of said incident light beam to form a reflected light beam;

modulating at a modulation frequency the polarization of at least one of said incident light beam and said reflected light beam;

nulling said reflected light beam by interacting said incident light beam or said reflected light beam with an analyzer and adjusting the analyzer transmission axis, $\theta_{PL}$, wherein said adjustment minimizes an even modulation frequency harmonic of said reflected light beam intensity;

without further adjustment of $\theta_{PL}$, illuminating a second sample at said oblique incidence angle with said incident light beam, said second sample reflecting at least some of said incident light beam to form a second reflected light beam; and determining a magnitude of an even modulation frequency harmonic of said second reflected light beam intensity, wherein said magnitude corresponds to an optical absorption coefficient difference between said first and said second samples.

In still another aspect, the invention provides for a method of determining an optical absorption coefficient difference between two samples, the method comprising illuminating a first sample at a near-normal incidence angle with an incident light beam having a right-circularly polarized component and a left-circularly polarized component, said first sample reflecting at least some of said incident light beam to form a reflected light beam;

modulating at a modulation frequency the polarization of at least one of said incident light beam and said reflected light beam;

nulling said reflected light beam by interacting said incident light beam or said reflected light beam with an analyzer and adjusting the analyzer transmission axis, wherein said adjustment minimizes an even modulation frequency harmonic of said reflected light beam intensity;

without further adjustment of the analyzer, illuminating a second sample at said near-normal incidence angle with said incident light beam, said second sample reflecting at least some of said incident light beam to form a second reflected light beam; and determining a magnitude of an even modulation frequency harmonic of said second reflected light beam intensity, wherein said magnitude corresponds to an optical absorption coefficient difference between said first and said second samples.

In one aspect of the invention, the first sample corresponds to a known control sample, and the second sample corresponds to an unknown sample. In another aspect, the known control sample is a blank sample. In yet another aspect, the first and second samples are located in discrete spatial regions, while in another aspect, the first and second samples are located in the same spatial region and the measurements of said first and said second samples are taken at different time points.

In another aspect, the invention provides for devices for determining a refractive index difference, an optical absorption coefficient difference, or both refractive index difference and optical absorption coefficient difference between two samples according to one or more of the above methods, said device including components adapted to carrying out one or more of the above method steps.

These and other advantages of the present invention will now be described with reference to the drawings and written description which are intended to exemplify but not limit the invention. Variations and departures from the exemplified embodiments will be obvious to persons of skill in the art and are intended to be within the spirit of the invention, the scope of which is to be limited only by the claims. All references to patents, publications and other materials are hereby incorporated by reference in their entirety for all purposes.

BRIEF DESCRIPTION OF THE DRAWINGS

FIG. 3(a) shows $\text{Im}\{\Delta_p - \Delta_s\}$. FIG. 3(b) shows $\text{Re}\{\Delta_p - \Delta_s\}$ for same region as shown in FIG. 3(a). FIG. 3(c) shows $\text{Im}\{\Delta_p - \Delta_s\}$ for another region of same microarray as shown in FIGS. 3(a) and 3(b), but where none of the Cy5-labeled cDNA hybridized. FIG. 3(d) shows $\text{Re}\{\Delta_p - \Delta_s\}$ for same region as shown in FIG. 3(c).

DETAILED DESCRIPTION OF PREFERRED EMBODIMENTS

Definitions

Figure 1:
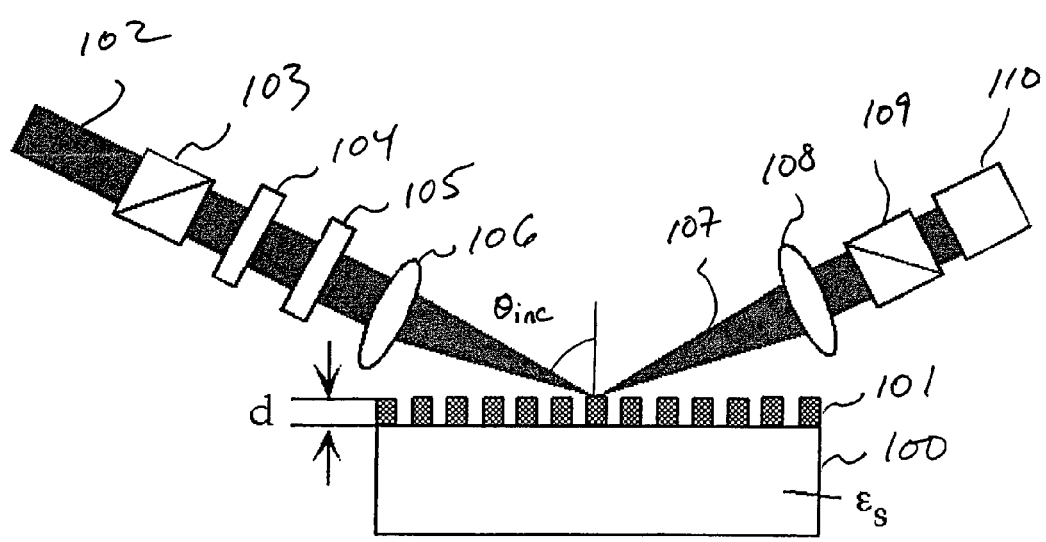
FIG. 1 diagrams an example of an instrument for carrying out the methods of the invention.

All terms, unless specifically defined below, are intended to have their ordinary meanings as understood by those of skill in the art. Masses and volumes are intended to encompass variations in the stated quantities compatible with the practice of the invention. Such variations are contemplated to be within, e.g. about ±10–20 percent of the stated quantities. In case of conflict between the specific definitions contained in this section and the ordinary meanings as understood by those of skill in the art, the definitions supplied below are to control.

"Interacting" a light beam with a component encompasses all manner of reflection, transmission, scattering, and combinations thereof. The particular modality of interaction is determined by the choice of the component and the desired effect on the properties of the light beam brought about by the interaction.

"Adjusting" an analyzer or a polarizer refers to changing the orientation of the analyzer or the polarizer.

A "biological molecule" encompasses any molecule synthesized or found within a biological cell including by way of example but not limitation, a protein, a nucleic acid, a carbohydrate, and a lipid.

An "incident light beam" refers to a light beam that has not reflected off a sample.

A "reflected light beam" refers to a light beam that has reflected off a sample.

The optical ellipsometry techniques of the present invention provide ways to measure differences in the refractive index and optical absorption coefficients of two samples. An advantage of the present invention over the prior art is that the methods of the invention include one or more nulling steps that render the methods sufficiently sensitive to measure differences between samples corresponding to the addition, removal, replacement or alteration of as small as a few percent or less of the atoms or molecules in a monoatomic or monomolecular layer of a sample or equivalent changes. The methods of the invention also allow for the detection of quite subtle structural, electronic, magnetic, or other alterations that affect a substantial portion of the atoms or molecules present in a monoatomic or monomolecular layer of a sample.

Thus, the methods are sufficiently sensitive to detect, e.g., molecular binding events such as nucleic acid hybridizations, protein-protein interactions, protein-nucleic acid interactions, conformation changes in macromolecular structures, and the addition, deletion, replacement or alteration of a few percent of a monolayer mass to the surface of a sample. The methods thus find broad applicability to monitoring biochemical and other binding events and in some instances can supplement or replace monitoring techniques that use specialized labels such as fluorophores to follow these events. While these advantages of the invention have been described with reference to alterations occurring within monoatomic or monomolecular layers of a sample, the methods of the invention are equally applicable to bulk samples. Similarly, while the advantages of the present invention have been described with reference to biological macromolecules such as nucleic acids, proteins, etc., the methods are applicable to the study of non-biological materials such as organic and inorganic crystal growth, corrosion, interfacial chemical reactions, electrochemical deposition, etc.

The samples may comprise any material whatsoever provided the sample materials interact with light to produce a change in the fractional reflectivity between polarized components of light interacting with the samples. Thus the samples may comprise non-chiral and non-magnetic materials or materials whose chiral and magneto-optic effects can be neglected for the application of interest. For these types of samples (Class I samples), the method preferably is practiced using oblique-incidence geometry. In other embodiments, the samples may comprise chiral or magnetic materials whose chiral or magneto-optic properties are of interest. For these types of samples (Class II samples), the method preferably is practiced using normal or near-normal incidence geometry. In a preferred embodiment, the two samples comprise two different spatial regions such as two different regions of an array of features, such as, e.g., an array of nucleic acids or an array of proteins, or any other type of array, although the methods of the invention are not limited to arrays. We refer to these as samples that are displaced in space. A first sample may comprise a blank or control region lacking a material of interest, while a second sample may comprise a region comprising a material of interest that an investigator wishes to detect or characterize. Of course, the method is equally applicable to two different regions both having materials of interest.

In another preferred embodiment, the two samples comprise the same spatial region that differs in composition as a function of, e.g., time. Thus measurements may be made from the same region at two different points in time, to compare the optical properties of the two samples according to the methods of the invention. We refer to these as samples that are displaced in time. In this case, the methods of the invention are used to determine whether there has been a change in the optical properties of that region over time. Such changes can be indicative of, e.g., an alteration of protein conformation, a molecular binding event, such as a nucleic acid hybridization event or a protein-protein or protein-nucleic acid binding event, or a molecular dissociation event indicating the disruption of a molecular complex. Thus, the methods of the invention are useful for following biochemical reactions, including reactions carried out using small quantities of materials such as the quantities bound to microarrays.

Using a gene chip as an example of Class I samples, single-stranded segments of "reference" nucleic acids such as deoxyribonucleic acids (DNAs) or ribonucleic acids (RNAs) can be deposited or fabricated on a substrate in the form of a two-dimensional array of "features" or patches. Subsequently, these "reference" nucleic acids are allowed to hybridize with single-stranded segments of a sample nucleic acid such as a sample DNA or RNA. By labeling the sample DNA with one or more fluorescent dyes or fluorophores, the binding affinity or the degree of hybridization can be read out in the form of a fluorescence yield using a confocal fluorescence microscope.

Although fluorescence labeling is widely used, the process is not always efficient or specific or non-intrusive enough to ensure adequate sensitivity, contrast, and fidelity. For example, photo-bleaching by the illuminating light or ambient light can render fluorescence-labeled samples and/or hybridized chips difficult to handle. Photobleaching also can make it impractical to reexamine features on a gene chip. Furthermore, variations may occur during deposition or in situ fabrication of the "reference" nucleic acid and in the subsequent hybridization process. As a result, a straight-forward interpretation of the fluorescence yield as an indicator of the binding affinity of the sample nucleic acid or extent of hybridization may not always be possible. These difficulties may be overcome using the methods of the invention insofar as the methods may be practiced using unlabeled materials or using stable, non-fluorescent labels.

We refer to the methods of the invention used in conjunction with Class I samples as an oblique-incidence optical reflectivity difference technique (OI-RD), that (1) complements and in some cases replaces scanning fluorescence microscopes; (2) has multiple contrast modes that can be used to verify the extent of molecular binding or dissociation events such as, e.g., nucleic acid hybridization, protein/nucleic acid interactions, or protein-protein interactions; and (3) has the sensitivity to detect changes in a sample as small as a few percent of one monoatomic or monomolecular layer of a sample.

In one embodiment, the methods of the invention measure the difference in fractional reflectivity change between the transverse electric ("TE" or "s-polarized") and transverse magnetic ("TM" or "p-polarized") components of an obliquely incident light. By obliquely incident, we mean incident light that is not normal nor near-normal to the plane of a surface comprising a sample. The essence of OI-RD is as follows.

Let $r_{p0}=|r_{p0}|\exp(i\Phi_{p0})$ and $r_{s0}=|r_{s0}|\exp(i\Phi_{s0})$ be the reflection coefficients for p- and s-polarized light from a substrate surface having a first sample. In one preferred embodiment this first sample is a control sample that is known to lack a material of interest, e.g., the sample consists of the substrate only and not the material of interest. Let $r_p=|r_p|\exp(i\Phi_p)$ and $r_s=|r_s|\exp(\Phi_s)$ be the reflection coefficients for p- and s-polarized light from a substrate surface having a second sample. In this preferred embodiment, the second sample comprises the substrate and a material of interest.

We measure the fractional reflectivity change $\Delta r/r_0=(r-r_0)/r_0$ in the p- and s-polarized components of a light impinging on the sample at an oblique angle of incidence. We define $S_N$ as the magnitude of the s-polarized component and $P_N$ as the magnitude of the p-polarized component. These magnitudes will be used below in describing conditions that must be met to practice this and other embodiments of the invention. In a preferred embodiment, oblique-incidence confocal imaging optics such as are shown in FIG. 1 are used, although any system having optical components capable of providing adequate spatial resolution and brightness may be used in accordance with the methods of the invention. In this preferred embodiment, a collimated monochromatic or monochromatized light source is used, although it is not crucial that monochromatic or monochromatized light be used. What is required is that, as explained below, the phase lag, $\phi$, can be adjusted so that an odd harmonics of the reflected light is minimized when the first sample is being illuminated. Thus, if a broad band phase-shifter such as a Fresnel rhomb achromatic retarder (Thermo Electron Corporation, Waltham, Mass.) with variable incidence angle is used, the requirement for monochromaticity may be relaxed completely.

In a preferred embodiment, the incident light beam with intensity $I_{inc}$ is initially p-polarized or s-polarized. The general condition that must be met, however is that the incident light beam has an initial linear polarization with $S_1 \neq P_1$. The polarization of the beam is altered at a frequency $\Omega$ with a polarization modulator such as a photoelastic modulator, (e.g., model PEM-90, Hinds Instruments, Inc. Hillsboro, Oreg.), or an electro-optic phase modulator, (e.g., models 4001, 4002, 4003, 4004, 4421, 423, 4431, or 4433 available from New Focus, Inc. San Jose, Calif.), or any other device that will alter the polarization from the initial linear polarization to a combination of the initial linear polarization and a polarization that includes an orthogonal component missing from the initial linear polarization.

For example, if the light beam is initially p-polarized, then the polarization modulator is used to add an s-polarization component to the beam, and to switch at frequency $\Omega$ between the initial p-polarized light and light having an s-polarization component. Similarly, if the light beam is initially s-polarized, then the polarization modulator is used to add a p-polarized component to the beam, and to switch at frequency $\Omega$ between the initial s-polarized light and the light having a p-polarized component. Let $S_2$ and $P_2$ be the magnitudes of the s-polarization and p-polarization components of the polarization-modulated beam. The general condition that must be met for the polarization-modulated beam is that $$\frac{S_1}{P_1} \neq \frac{S_2}{P_2}.$$

The relative amounts of s-polarization and p-polarization components present in the initial linear polarization and in the modulated polarization may vary depending on the application for which the method is used. What is required is that the $S_1 \neq P_1$ and $$\frac{S_1}{P_1} \neq \frac{S_2}{P_2}$$

conditions set forth above are chosen to yield adequate signal-to-noise ratios in the even and odd harmonics of the reflected light, as described below. For example, an initially p-polarized beam ($S_1=0$, $P_1 \neq 0$) may be switched by a modulator completely to an s-polarized beam ($S_2 \neq 0$, $P_2=0$) or be switched to a nearly p-polarized beam with a small s-polarization component ($P_1 \approx P_2$ but $P_2 >> S_2$). This will, of course, vary depending on, e.g., the instrumentation used for detection of the reflected light, and the nature of the samples under investigation, and can be readily determined by an ordinarily skilled person.

Polarization modulation may be done in a continuous or a discrete manner. By continuous modulation, we mean the change in polarization is continuous in time, such as that produced by a photo-elastic modulator, an electro-optic modulator, or a wave plate on a continuously rotating wheel. Discrete modulation refers to use of a discrete set of mixed polarizations chosen to obtain the even and odd "harmonics" algebraically, as described in greater detail below.

The polarization-modulated beam is then passed through a phase shifting device such as a voltage-controlled Pockel cell (Cleveland Crystals, Highland Heights, Ohio), or a mechanically controlled Soleil-Babinet compensator (Coherent Inc., Auburn, Calif.; Cleveland Crystals Inc., Highland Heights, Ohio), or a Berek compensator (New Focus, San Jose, Calif.), or a double-Fresnel rhomb achromatic retarder (Thermo Oriel, Stratford, Conn.; Halbo Optics, Chelmsford, UK) so that a variable phase lag, $\phi$, can be added to the s-polarized component, relative to the p-component. The beam is subsequently focused on the first sample surface at an oblique incident angle $\theta_{inc}$. The reflected beam is recollimated and sent through an analyzing polarizer (also referred to as a polarization analyzer or analyzer) such as, e.g., a Glan laser double escape window polarizer, model CPAD (CVI Laser, Albuquerque, N. Mex.) or Glan-Thompson polarizer model 5524 (New Focus, San Jose, Calif.), the analyzer having its transmission axis set at angle $\theta_{PL}$ from the s-polarization axis.

The resulting intensity of the reflected, analyzed beam, $I_R(t)$ is detected using, e.g., a photomultiplier, or a diode based photodetector such as a biased silicon photodiode, or any other device capable of transducing light intensity into a variable electrical signal. $I_R(t)$ has a time invariant component $I_R(0)$ that is the mean intensity of the reflected light, as well as terms that vary with time at various harmonics of the modulation frequency $\Omega$.

The odd and even harmonics $I_R(N\Omega)\cos[(N\Omega)t]$ for N=odd and N=even, respectively are detected by analyzing the signal output from the light transducer device using a lock-in amplifier such as a National Instrument Dynamic Signal Acquisition Module (model NI-4472 for PCI or PXI) controlled with for example National Instruments LabVIEW Software and the Lock-In Amplifier Start-up Kit available from National Instruments (Austin, Tex.), or models SR810, or SR830, or SR844, or SR850, or SR530, or SR510 available from Stanford Research Systems (Sunnyvale, Calif.), or models 7280, or 7265, or 7225, or 7225BFP, or 7220BFP, or 5105, or 5106, or 5110 A, or 5209, or 5210 available from Perkin Elmer Instruments (Oak Ridge, Tenn.), or a spectrum analyzer such as an ESA-L series portable spectrum analyzer, or an ESA-E series portable spectrum analyzer, or an 8560E series portable spectrum analyzer, or an 8590 series portable spectrum analyzer or a PSA series high-performance spectrum analyzer, or an MMS modular measurement system, or swept-tuned spectrum analyzer available from Agilent (Palo Alto, Calif.), or any other device or method capable of detecting with sufficient signal-to-noise ratios spectral components of the varying signal output from the light transducer device. For example, the harmonics can be obtained by digitizing the signal, such as, e.g., a photodiode or photomultiplier current, loading the digitized signal into a computer, Fourier transforming the digitized signal using, e.g., an FFT algorithm, to obtain the power spectrum of the signal, and determining the power of a frequency component corresponding to an odd or even harmonic of the modulation frequency, $\Omega$.

One of the key aspects of the invention is that when the incident beam illuminates the first sample, $\theta_{PL}$ is adjusted such that the intensity of an even harmonic of the reflected analyzed beam, $I_R(N\Omega)$, is minimized (N=even), and the phase lag $\phi$ is adjusted such that the intensity of an odd harmonic of the reflected analyzed beam, $I_R(N'\Omega)$, is minimized (N'=odd). We refer to these minimization steps as "nulling" steps. In a preferred embodiment, N=even=2, and $\theta_{PL}$ is adjusted such that $I_R(2\Omega)=0$, and N'=odd=1 and $\phi$ is adjusted such that $I_R(\Omega)=0$. In this preferred embodiment, for substrates that are transparent or minimally absorptive, when the incident beam illuminates a second sample, the subsequent changes in $I_R(\Omega)$ and $I_R(2\Omega)$ arise respectively from differences in refractive index and optical absorption coefficient between the first and second samples.

Thus, if the first sample consists of a transparent substrate only and not a material of interest, such as a glass surface, and the second sample comprises a material of interest, e.g., a region of nucleic acid on the glass substrate, then the changes in $I_R(N\Omega)$ for N=odd and N=even between the two samples come from the change in refractive index and optical absorption coefficient from those of the substrate to those of the nucleic acid, or whatever substance is bound or adsorbed to the substrate. The refractive index and optical absorption coefficient of the substance are derived from $\Delta_p-\Delta_s$ where $\Delta_p=(r_p-r_{p0})/r_{p0}$ and $\Delta_s=(r_s-r_{s0})/r_{s0}$. The real and imaginary parts of $\Delta_p-\Delta_s$ are determined from the following measurement, $$I_R(N\Omega) \cong c_1(N) I_{inc} |r_{p0} \sin \theta_{PL}|^2 Im\{\Delta_p-\Delta_s\} \text{ for } N=\text{odd} \quad (1)$$

$$I_R(N\Omega) \cong c_2(N) I_{inc} |r_{p0} \sin \theta_{PL}|^2 Re\{\Delta_p-\Delta_s\} \text{ for } N=\text{even} \quad (2)$$

$c_1(N)$ and $c_2(N)$ are two unit-less numerical constants that depend on N and how the initial polarization is modulated. It can be shown that on a transparent substrate such as a glass slide, the odd harmonics, $I_R(N\Omega)$ for N=odd, or $Im\{\Delta_p-\Delta_s\}$ is a measure of the variation of refractive index, while the even harmonics, $I_R(N\Omega)$ for N=even, or $Re\{\Delta_p-\Delta_s\}$ is a measure of the variation of the optical absorption coefficient.

The real and imaginary parts of $\Delta_p-\Delta_s$ characterize the material of interest relative to the substrate which is used to null the harmonics. For this reason, it may be advantageous to eliminate the system dependent factors $c_1(N)I_{inc}|r_{p0} \sin \theta_{PL}|^2$ and $c_2(N)I_{inc}|r_{p0} \sin \theta_{PL}|^2$ in front of $(\Delta_p-\Delta_s)$. To obtain the factor in front of $Im\{\Delta_p-\Delta_s\}$, the beam is focused on the first sample and the phase lag $\phi$ is adjusted so that the detected beam intensity at the odd harmonic is maximized, and the maximum strength of the detected signal so obtained is equal to $c_1(N)I_{inc}|r_{p0} \sin \theta_{PL}|^2$. To obtain the factor in front of $Re\{\Delta_p-\Delta_s\}$, the even harmonic is nulled in the region of the first sample, and a second analyzer having its transmission axis oriented along either the p-polarization or s-polarization axis is inserted in the light path immediately before or immediately after the sample. For the embodiment illustrated in FIG. 1, this corresponds to inserting the second analyzer into the light path in a region between either of the two lenses 106 and 107 and the sample. The detected beam intensity at the even harmonic is equal to one half of $c_2(N)I_{inc}|r_{p0} \sin \theta_{PL}|^2$, multiplied by the transmittance of the second polarizer for the passing polarization component. There are other methods to obtain these two factors, as will be recognized by those of ordinary skill in the art.

Note that if the material of interest is on a substrate that is not transparent, i.e., a substrate that absorbs light, the refractive index and the optical absorption coefficients of the material of interest are not separately determined from the odd and even harmonics of the detected light intensity as described above. Rather, algebraic methods must be used to determine these two parameters using both odd and even harmonics information, as set forth in the attached appendix.

In carrying out the methods of the invention, one of ordinary skill will readily appreciate how to select a harmonic that provides adequate signal-to-noise properties. While in principle, all odd harmonics provide equivalent information about variation in refractive index, and all even harmonics provide equivalent information about variation in optical absorption coefficient, it can fortuitously arise that e.g., the first harmonic is in a noisy region of the spectrum because of, e.g., instrument or environment noise, and so the third or fifth or higher-order odd harmonic should be obtained for purposes of evaluating refractive index variations.

The relative signal strengths of various harmonics can be adjusted, if necessary, by, e.g., varying the depth of polarization modulation. In most cases, the values of the first through seventh order odd harmonics can be made to have values within a factor of two of each other, and similarly, the values of the second through eighth order even harmonics also can be made to have values within a factor of two of each other. This offers sufficient flexibility for most practical applications of the methods of the invention.

As one of skill in the art readily will appreciate, subsequent sample regions can be interrogated using the above-described techniques, and the odd and even harmonics will show the differences in the refractive index and optical absorption coefficient between the first and subsequently interrogated sample regions.

If a sample is labeled with a dye and monochromatic light having a wavelength within the dye's absorption band is used in the method, then a scan of the sample to determine an even harmonic as a function of location will provide an indication of the relative amounts of dye in the interrogated locations. For purposes of illustration, consider a nucleic acid array hybridized with a fluorescent-labeled nucleic acid. According to the methods of the invention, a scan of the array surface to obtain an even harmonic using a wavelength corresponding to the absorption band for the fluorescent dye will provide information roughly equivalent to a fluorescence yield scan of the array obtained using a fluorescence microscope. That is, the even harmonic will provide information that corresponds to the location and amount of labeled nucleic acid present on the array. Compared to fluorescence microscopy, though, the methods of the invention have the advantage of not relying on fluorescence yield of a fluorophore which can vary as a result of quenching or photobleaching phenomena, but instead on the absorption properties of the dye, which tend to be more stable than the emission properties.

For purposes of illustration, consider the same type of array hybridized with an unlabeled nucleic acid sample and illuminated with light at a wavelength other than an absorption band wavelength for the nucleic acid. A scan of the array surface according to the methods of the invention to obtain an even harmonic will not detect features on the array surface. However, a scan of the array surface to obtain an odd harmonic will show variations in refractive index along the surface of the array. This variation corresponds to the surface density of nucleic acid along the array surface, and so provides a convenient way to measure, e.g., hybridization of even an unlabeled nucleic acid to the array. See Appendix Special Case 4. Similarly, an odd harmonic scan can be used to examine the array prior to hybridization to ensure the quality of the array. Because the method is non-destructive, an array can be repeatedly scanned using the methods of the invention. This is in contrast to fluorescence-based methods in which repeated scans can lead to signal loss due to photo-bleaching.

The embodiment illustrated in FIG. 1 makes use of spherical lenses (106, 108) for the focusing optics so that a small spatial region i.e., a spot, is illuminated and the reflected light from the illuminated region is analyzed to obtain one or more of the harmonics. In some applications, such as those involving the use of two-dimensional arrays, it is advantageous to analyze a line of features on the array at once, rather than sequentially analyzing each feature within the line. The advantage in time saving can be as much as N-fold, where N is the number of spots within a line. For high-density oligonucleotide arrays or chips, the amount time required to analyze the features on the chip can be reduced by as much as 1000-fold using line analysis in lieu of spot analysis. Line analysis can be carried out using cylindrical lenses as the focusing optics (106) on the illumination side. On the reflection side, spherical optics (108) may be used to image the reflected beam onto a linear detector array (110) such as a linear diode array instead of a single detector.

It also is possible to use a two-dimensional (2D) detector array such as a charge-coupled device (CCD) detector or a 2D image intensifier to analyze a two-dimensional array of features simultaneously. A two dimensional area is illuminated and the light reflected from the illuminated area is focused on the two-dimensional detector to form an image of the illuminated area. Spectral analysis of the signals arising from the discrete regions of the two dimensional detector is carried out according to the methods of the invention to obtain the desired harmonics.

In addition to the methods described above, other techniques can be used by one of ordinary skill to practice the invention. For example, the polarization modulation has been described above by reference to electro-optic and photo-elastic modulation. In addition, one of ordinary skill will appreciate that other methods can be used for polarization modulation such as, e.g., mechanical rotation of a wave plate having any arbitrary phase retardation between two orthogonal polarizations, or a double-Fresnel rhomb mounted on a spinning wheel or rotation stage. Polarization modulation also can be carried out by reflecting the beam off one or more sets of surfaces or using a combination of transmission and reflection optics. An example of using a reflection geometry to obtain the polarization modulation is use of a double-Fresnel rhomb or one or a pair of reflecting surfaces mounted on a spinning wheel.

Another embodiment of the method also can be practiced using the same setup as described above with the variation that the phase-shifter is placed after the sample, and before the analyzer. The requirements that $S_1 \neq P_1$ and $$\frac{S_1}{P_1} \neq \frac{S_2}{P_2}$$

pertain to this embodiment as well.

In lieu of polarization modulation of the incident beam, the polarization modulation can be introduced after the beam has been reflected off a sample surface. In this embodiment, the arrangement of the optics is reversed with respect to what is shown in the embodiment illustrated in FIG. 1. Thus, a light beam is passed through an analyzer having its transmission axis oriented at $\theta_{PL}$ with respect to the s-polarization axis; the resultant beam is used to illuminate the sample surface at an oblique incidence angle $\theta_{inc}$, and forms a reflected beam; the reflected beam then is passed through a phase-shifter such as, e.g., a Pockel cell to introduce a phase lag between the s- and p-polarized components of the reflected beam; the reflected beam to which the phase lag has been added is then polarization modulated by passing the phase-lagged, reflected beam through a device such as an electro-optic or photo-elastic modulator, or a rotating wave plate, or a double Fresnel rhomb mounted on a spinning wheel or rotation stage as described above so that the polarization of the beam is periodically or discretely modulated.

The resultant beam then is passed through a polarizer that passes an unequal combination of p-polarization and s-polarization components or is passed through or reflected off any device so that either of the s- or p-polarized components or an unequal combination of the s- and p-polarized components of the beam is detected by a detector. In this way, the odd harmonic after nulling by adjustment of the phase lag will measure $\text{Im}\{\Delta_p - \Delta_s\}$, and the even harmonic after nulling by adjustment of the analyzer's transmission axis, namely, $\theta_{PL}$, will measure $\text{Re}\{\Delta_p - \Delta_s\}$ between two samples displaced in space or time.

The conditions for embodiments in which the polarization modulation is introduced after the beam has interacted with the sample are as follows. The initial beam need not but may be linearly polarized. An arbitrary initial polarization is sufficient. It also is required that a sufficient amount of light pass through the analyzer to provide adequate signal-to-noise ratios for practice of the invention. As discussed above, the amount of light required to provide adequate signal-to-noise ratios will vary depending upon the details of the sample and system components used, and can readily be determined by one of ordinary skill in the art. Once the beam passes through the phase-shifter, it emerges with s-polarization and p-polarization component magnitudes $S_1$ and $P_1$. After passing through the polarization modulator, the beam emerges with s-polarization and p-polarization component magnitudes $S_2$ and $P_2$. The necessary condition is that $$\frac{S_1}{P_1} \neq \frac{S_2}{P_2}.$$

It also is a necessary condition that the polarizer's transmission axis is not oriented at ±45° with respect to the s-polarization axis.

In another variation of methods in which polarization modulation is introduced after the beam has been reflected off a sample surface, the phase-shifter is placed between the analyzer and the sample, and the s-polarization and p-polarization component magnitudes $S_1$ and $P_1$ are characteristic of the beam after it has interacted with the sample.

Two additional embodiments employing an initially elliptically polarized beam also are within the scope of the present invention. In the first "elliptically polarized" embodiment, the setup comprises, in order, a light beam with an initial elliptical polarization (preferably the source of this beam is a laser), a device that variably changes the relative magnitude of the s-polarization component to the p-polarization component (serving as the analyzer) (e.g., a wave plate, or a double Fresnel rhomb, or a mirror, or a set of mirrors, or a transparent material, or a set of transparent materials), sample, phase-shifter through which the beam emerges with s-polarization and p-polarization component magnitudes $S_1$ and $P_1$, polarization modulator through which the beam emerges with s-polarization and p-polarization component magnitudes $S_2$ and $P_2$ with the necessary condition that $$\frac{S_1}{P_1} \neq \frac{S_2}{P_2},$$

polarizer with its transmission axis not oriented at ±45° with respect to the s-polarization axis, and detector. The second "elliptically polarized" embodiment differs from the first "elliptically polarized" embodiment in that the positions of the sample and phase-shifter are reversed and that the s-polarization and p-polarization component magnitudes $S_1$ and $P_1$ are characteristic of the beam after it has interacted with the sample.

To summarize, the methods of the invention for use with Class I materials have been described above with respect to six different optical setups:

Setup 1: light source with initial linear polarization, polarization modulator, phase-shifter, sample, analyzer, detector Setup 2: light source with initial linear polarization, polarization modulator, sample, phase-shifter, analyzer, detector Setup 3: light source with arbitrary initial polarization, analyzer, sample, phase-shifter, polarization modulator, polarizer, detector Setup 4: light source with arbitrary initial polarization, analyzer, phase-shifter, sample, polarization modulator, polarizer, detector Setup 5: light source with initial elliptical polarization, analyzer, sample, phase-shifter, polarization modulator, polarizer, detector Setup 6: light source with initial elliptical polarization, analyzer, phase-shifter, sample, polarization modulator, polarizer, detector Nulling of the first order or odd harmonics has been described above by reference to electro-optic devices such as a Pockel cell or variable wave plates such as a Babinet compensator, a Soleil compensator, or a Berek compensator. However, one of ordinary skill can carry out the first order or other odd harmonic nulling step using a device based upon photo-elastic effect such as a mechanically driven photoelastic modulator or a tilted uniaxial or bi-axial wave plate such that the optical path for the two orthogonal polarized components (i.e. the p-polarization and the s-polarization components) can be changed to obtain the desired phase lag.

If the second or other even order harmonic is not required for purposes of the analysis being carried out according to the methods of the invention (i.e., if optical absorption coefficient variations are not to be obtained), then the nulling step for the second or other even order harmonic can be skipped, and instead, the transmission axis of the analyzer can be set to any angle $\theta_{PL}$ other than the two orthogonal angles that allow transmission only of the p-polarized or the s-polarized components. For practicing the embodiments of the invention that do not require determination of even order harmonics, the analyzer can be replaced with any optical device (such as a tilted, transparent optical window in the beam path such that the incidence plane to the window bisects the s-polarization and the p-polarization axes) or other optical arrangements that will mix the s-polarized and the p-polarized components before the beam reaches the detector.

Second or other even order harmonics also may be nulled using methods other than adjustment of the transmission axis of the analyzer as described above. For example, any optical device that can change the relative amplitudes of the s-polarized and the p-polarized components of a light beam, either in transmission mode, in which the light beam passes through the device, or in reflectance mode, in which the light beam is reflected off one or a set of surfaces having different reflectivities for the s-polarized and the p-polarized components may be used. An example of this is provided in A. Wong and X. D. Zhu, "An optical differential reflectance study of adsorption and desorption of Xenon and Deuterium on Ni(111)," *Appl. Phys. A* 63, 1 (1996), which is hereby incorporated by reference in its entirety for all purposes.

The periodic polarization modulation may also be eliminated altogether and one can make measurements using a discrete set of mixed polarizations chosen to obtain the even and odd "harmonics" algebraically. This may be advantageous for imaging one line at a time or the entire area of the interrogated sample surface with a low dc noise detector such as a cooled CCD. In this case, for example, one can pass the initial light beam through, say, a quarter-wave plate, or any wave plate other than a half-wave plate. Let $\phi$ be the angle between the initial linear polarization and one of the principal axes of the wave plate. One can measure the light intensity after the analyzer at $\phi=0$, $\pi/4$, and $3\pi/4$. Then, for transparent substrates or substrates with low light absorption, $[I_R(\phi=\pi/4)-I_R(\phi=\pi 3/4)]$ is proportional to $\text{Im}\{\Delta_p-\Delta_s\}$ after nulling with a phase shifting device such a Pockel cell following the above-described procedure or variations of it; while $[2I_R(\phi=0)-I_R(\phi=\pi/4)-I_R(\phi=3\pi/4)]$ is proportional to $\text{Re}\{\Delta_p-\Delta_s\}$ after nulling with the analyzing polarizer following the above-described procedure or variations of it.

A group of setups and constraints analogous to those described above may be used to practice embodiments of the invention with Class II materials, i.e., chiral or magnetic materials whose chiral or magneto-optic properties are of interest. For these setups, in lieu of an oblique incidence geometry, near-normal incidence geometry is used. A perfectly normal incidence geometry is not always practical as the illumination section of the setup will more often than not interfere with the detection section (see FIG. 1). Usually one way to overcome the problem is to use a near-normal incidence geometry. The criterion is that the contribution from the non-magnetic and non-chiral part of the material response through the now non-vanishing $\Delta_p-\Delta_s$ term is either small compared to the chiral or magneto-optic part of the response, or can be ascertained and then separated from the measurement. Preferably, near-normal incidence geometry includes angles that range ±10 degrees from the normal, or ±5 degrees from the normal, or ±2 degrees from the normal. In those circumstances in which the setup permits, near-normal incidence geometry will include setups that have a normal incidence angle. We define reflectivity constants $r_R$ for right circularly-polarized light component (analogous to constant $r_p$ for p-polarization component) and $r_L$ for left circularly-polarized light component (analogous to constant $r_s$ for s-polarization component) and let $R_N$ be the magnitude of the right circularly-polarized component and $L_N$ be the magnitude of the left circularly-polarized component. In the embodiments practiced with Class II materials, the phase-shifter is one that works with circularly-polarized light. In preferred embodiments the phase-shifter is a Faraday rotator or any material that in transmission or reflection mode can be used to add a relative phase difference to the R and L components of the polarized light. As with the Class I embodiments, for Class II material embodiments, nulling of the odd harmonics is carried out by adjusting the phase-shifter (e.g., Faraday rotator) so that the magnitude of the odd harmonic is minimized. In the Class II embodiments, a quarter-wave plate is used in conjunction with a conventional polarization analyzer. A quarter-wave plate is used because it converts the two circularly-polarized components into two orthogonal, linearly-polarized components without disturbing the magnitude and relative phase of the components. With Class II embodiments, nulling of the even harmonic is carried out by adjusting the orientation of the analyzer's transmission axis with respect to the quarter-wave plate so that the magnitude of the even harmonic is minimized.

With the analogies between Class I and Class II embodiments having been described above, we now describe six setups for practicing Class II embodiments of the invention.

In the first Class II setup, the initial beam has an elliptical polarization with components $R_1 \neq L_1$. The initial beam passes through a polarization modulator and emerges with components $R_2$ and $L_2$ with the necessary condition that $$\frac{R_1}{L_1} \neq \frac{R_2}{L_2}.$$

The beam then passes through a phase-shifter for circularly-polarized light, interacts with the sample, passes through a quarter-wave plate that converts two circularly-polarized components into two orthogonal, linearly-polarized components, then through the analyzer, and finally falls on the detector.

The second Class II setup has an initial elliptically polarized beam with components $R_1 \neq L_1$. The initial beam passes through a polarization modulator and emerges with components $R_2$ and $L_2$ with the necessary condition that $$\frac{R_1}{L_1} \neq \frac{R_2}{L_2}.$$

The beam then interacts, in sequence, with the sample, a phase-shifter for circularly-polarized light, passes through a quarter-wave plate that converts two circularly-polarized components into two orthogonal, linearly-polarized components, then through the analyzer, and finally falls on the detector.

The third Class II setup uses an initial light beam with an arbitrary initial polarization, passes the beam through an analyzer (requiring, of course, that a sufficient amount of light pass through the analyzer to provide adequate signal-to-noise ratios for practice of the methods of the invention), then through a first quarter-wave plate, interacts with the sample, then with the phase-shifter for circularly-polarized light and emerges with resultant components $R_1$ and $L_1$, then with the polarization modulator and emerges with components $R_2$ and $L_2$ with the requirement that $$\frac{R_1}{L_1} \neq \frac{R_2}{L_2}.$$

The beam then passes through a second quarter-wave plate that converts two circularly-polarized components into two orthogonal, linearly-polarized components, followed by a polarizer with the transmission axis oriented not parallel to either the slow axis (SA) or the fast axis (FA) of the second quarter-wave plate, and finally falls on the detector.

The fourth Class II setup uses an initial light beam with an arbitrary initial polarization, passes the beam through an analyzer (requiring, of course, that a sufficient amount of light pass through the analyzer to provide adequate signal to noise for practice of the methods of the invention), then through a first quarter-wave plate, followed by a phase-shifter for circularly-polarized light, after which the beam interacts with the sample, and emerges with resultant components $R_1$ and $L_1$. The beam then interacts with the polarization modulator and emerges with components $R_2$ and $L_2$ with the requirement that $$\frac{R_1}{L_1} \neq \frac{R_2}{L_2}.$$

The beam then passes through a second quarter-wave plate that converts two circularly-polarized components into two orthogonal, linearly-polarized components, followed by a polarizer with the transmission axis oriented not parallel to either the slow axis (SA) or the fast axis (FA) of the second quarter-wave plate, and finally falls on the detector.

In the fifth Class II setup, the initial beam has an elliptical polarization, it interacts with a device that variably changes the relative magnitude of the right-circular polarization component, R, to the left-circular polarization component, L, for example, a circularly dichroic material with a variable thickness in transmission mode; such a material absorbs or transmits (as a result of absorption) the left-circularly polarized light and the right-circularly polarized light differently, and serves the same purpose as the analyzer quarter-wave plate combination described above, interacts with the sample, and then with a phase-shifter for circularly-polarized light and emerges with resultant components $R_1$ and $L_1$. The beam then interacts with the polarization modulator and emerges with components $R_2$ and $L_2$ with the requirement that $$\frac{R_1}{L_1} \neq \frac{R_2}{L_2}.$$

The beam then passes through a quarter-wave plate that converts two circularly-polarized components into two orthogonal, linearly-polarized components, followed by a polarizer with the transmission axis oriented not parallel to either the slow axis (SA) or the fast axis (FA) of the quarter-wave plate, and finally falls on the detector.

In the sixth Class II setup, the initial beam has an elliptical polarization, it interacts with a device that variably changes the relative magnitude of the right-circular polarization component, R, to the left-circular polarization component, L, (serving the same purpose as the analyzer quarter-wave plate combination described above), interacts with the phase-shifter for circularly-polarized light, and then with the sample, and emerges with resultant components $R_1$ and $L_1$. The beam then interacts with the polarization modulator and emerges with components $R_2$ and $L_2$ with the requirement that $$\frac{R_1}{L_1} \neq \frac{R_2}{L_2}.$$

The beam then passes through a quarter-wave plate that converts two circularly-polarized components into two orthogonal, linearly-polarized components, followed by a polarizer with the transmission axis oriented not parallel to either the slow axis (SA) or the fast axis (FA) of the quarter-wave plate, and finally falls on the detector.

EXAMPLE 1

Characterization of Nucleic Acid Hybridization on a Microarray

Hybridized microarrays were prepared as follows. DNA fragments of 0.3 Kb length were synthesized by the polymerase chain reaction. An Affymetrix GMS-417 microarrayer (Affymetrix, Inc., Santa Clara, Calif.) was used according to the manufacturer's instructions to print an array on a poly-L-lysine treated glass slide having dimensions of 1.2 cm by 1.2 cm. The features are round spots having an average diameter of 100 microns and an average center-to-center separation of 180 microns. The printed DNA fragments were cross-linked to the poly-L-lysine coated glass surface by exposure to ultraviolet light. Approximately 1 pico-gram of DNA is printed per spot, giving rise to a density within a spot on the order of approximately $1 \times 10^{13}$ molecules/cm$^2$. The glass slide was then dried in vacuo. Non-specific binding sites were blocked by treating the slide with succinic anyhydride in a sodium borate solution. These steps were carried out following protocols published by Operon Technologies, Inc. "Protocol for Preparation of PLL Slides, Microarrays" (2001), "Procedure for Printing Slides, Microarrays" (2001), "Post Processing Protocol, Microarrays" (2001), Qiagen Operon Nev., incorporated herein by reference.

Prior to hybridization, the DNA fragments on the slide were denatured by immersing the slide in boiling water, followed by an immersion in 95% ethanol. The array was hybridized with Cy3-labeled cDNAs reverse transcribed from isolated RNA following the Operon Technologies, Inc. "Reverse Transcription, Microarrays" (2001) protocol, incorporated herein by reference. The labeled cDNA molecules are on the order of 0.5 Kb length. The Cy3-labeled cDNA was denatured and hybridized with the array at 42° C. overnight under standard conditions set forth in the Operon Technologies, Inc. "Hybridization Protocol, Microarrays" (2001) protocol, incorporated herein by reference. Following the hybridization step, the array was washed in 2×SSC, 0.2% SDS for approximately 1 minute, then in 0.2×SSC, and then in 0.05×SSC, following the Operon Technologies, Inc. "Hybridization Protocol, Microarrays" (2001) protocol to remove non-hybridized cDNA. The slide was dried prior to carrying out optical scanning, as described below.

Cy3 is a fluorescent dye having an absorption maximum at 550 nm and an emission maximum at 570 nm. The Cy3 dye attached to the hybridized cDNA was photo-bleached using a Spectra-Physics diode-pumped solid-state laser DPSS-532 (Spectra-Physics, Mountain View, Calif.) that delivers a continuous power of 100 milliwatts at 532 nm. The fluorescence-labeled features were exposed to a flux of 100 J/cm$^2$ ($3 \times 10^{20}$ photons/cm$^2$) which reduced the fluorescence yield of the dye by about a factor of $10^5$.

For an oblique-incidence reflectance-difference scan as illustrated in FIG. 1, we use a 5 milli-Watt linearly-polarized He—Ne laser (model LGK7654-7, LASOS, Ebersberg, Germany). The initial polarization is set along the s-polarization direction by passing the beam (102) through a polarizer (103) (model 5524, New Focus, San Jose, Calif.). The beam is passed through a photoelastic modulator (104) (model PEM90, Hinds Instruments, Hillsboro, Oreg.) with the initial polarization bisecting the two principal axes of the modulator. Periodically at $\Omega$=50 kHz, the polarization modulator produces an output polarization that is changed in a sequence of the original s-polarization, left circular polarization, p-polarization, left circular polarization, s-polarization, right circular polarization, p-polarization, right circular polarization, and finally back to s-polarization. The polarization-modulated beam is then passed through a phase-shifter (105), in this instance, a Pockel cell (model Impact 10, Cleveland Crystals, Highland Heights, Ohio) with the principal axes of the cell aligned parallel to s -and p-polarizations. The Pockel cell adds between the s- and p-polarized components a phase lag, $\phi$, that can be changed by applying an electrical voltage. The phase-lagged, polarization-modulated beam is focused through a lens (106) on a region of the slide having no DNA features. The reflected beam (107) is passed through a lens (108) and an analyzing polarizer (i.e., analyzer) (109) (model 5524, New Focus, San Jose, Calif.) with its transmission axis (TA) set an angle of $\theta_{PL}$ with respect to the s-polarization axis. The resultant beam with the intensity IR(t) is then detected with a biased silicon photodiode (110) (model 818-BB-40, Newport, Irvine, Calif.). The photo-current, in proportion to $I_R(t)$, is sent to two Lock-in amplifiers (model SR830, Stanford Research Systems, Sunnyvale, Calif.) to detect the first and second harmonics in the photo-current, or equivalently, $I_R(t)$.

We null (i.e., minimize the intensity of) the first harmonic by adjusting the voltage on the Pockel cell (105) and null the second harmonic by adjusting the orientation of the transmission axis of the analyzer (109). To obtain Im$\{\Delta_p-\Delta_s\}$, we measure the factor $c_1(N=1)I_{inc}|r_{p0} \sin \theta_{PL}|^2$ by adjusting the voltage on Pockel cell (105) until the detected first harmonic signal is maximized. We divide the subsequently measured first harmonic signal (i.e., after the initial nulling) by this maximum signal to deduce Im$\{\Delta_p-\Delta_s\}$ directly.

Figure 2:
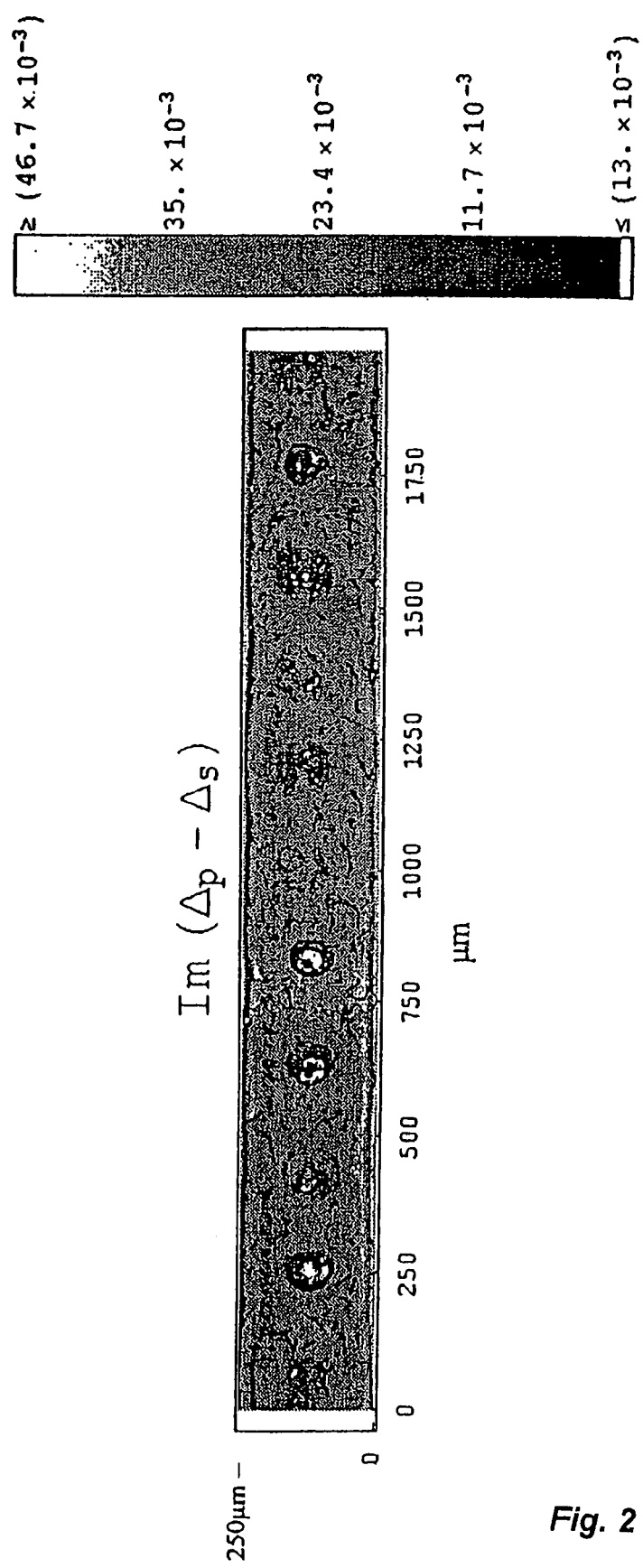
FIG. 2 illustrates an image scan using the first harmonics over an area of a hybridized gene chip.

During the scan, the illuminating optics and detection system were fixed, and the chip was translated by mounting it on top of two orthogonal translation stages (Newport-Klinger, model 462-XY, Irvine, Calif.). 80-pitch screws were attached to each of the stages and the translation stages were moved sequentially by turning the screws with stepper motors. The smallest achievable step size along both the x and y direction on the surface was 0.8 microns in this experiment. To generate the scan shown as FIG. 2, a 2.4 micron step size was used for x and y, as the size of the features in the array are on the order of approximately 40 steps or so (i.e. around 100 microns). FIG. 2 shows a plot of Im$\{\Delta_p-\Delta_s\}$ which was obtained as described above.

The plot of Im$\{\Delta_p-\Delta_s\}$ in FIG. 2 corresponds to refractive index changes that allow surface density variations of the features to be observed, which in turn, can be correlated to the extent of hybridization. The gray-scale variation reflects surface density changes from feature to feature. The lightest patch is the least hybridized single-stranded DNA patch, while the darkest patch is the most extensively hybridized. Also plainly visible is the feature-to-feature variation present in the array, which could significantly influence the interpretation of fluorescence yield measurements.

EXAMPLE 2

Characterization of Nucleic Acid Hybridization on a Two-Dimensional Microarray An Affymetrix GMS-417 microarrayer (Affymetrix, Inc., Santa Clara, Calif.) was used according to the manufacturer's instructions to prepare arrays of features using a variety of different 60-mer DNA oligonucleotides ("60-mer oligos") purchased from Sigma-Genosys (The Woodlands, Tex.). The sequences of the 60-mers were designed so that a subset was predicted to hybridize with the population of cDNAs used in the hybridization experiment. The 60-mer oligos were printed on poly-L-lysine coated glass slides using the GMS-417 microarrayer, and were then cross-linked to the poly-L-lysine coated glass surface by exposure to ultraviolet light. The slides subsequently were processed with succinic anyhydride in a sodium borate solution to block out non-specific binding sites. The printing, cross-linking, and post-processing steps were carried out following protocols published by Operon Technologies, Inc. "Protocol for Preparation of PLL Slides, Microarrays" (2001), "Procedure for Printing Slides, Microarrays" (2001), "Post Processing Protocol, Microarrays" (2001), Qiagen Operon N.V., incorporated herein by reference. The printed features are circularly shaped with a bi-lobular fine structure, have diameters of 130 microns and an average center-to-center separation of 190 microns. The bi-lobular structure results from a shape modification of the GMS-417 transfer tip.

The array was subsequently hybridized with Cy5-labeled cDNAs reverse transcribed from isolated RNA following the Operon Technologies, Inc. "Reverse Transcription, Microarrays" (2001) protocol, incorporated herein by reference. The labeled cDNA molecules are on the order of 0.5 Kb length. The Cy5-labeled cDNA was first heat denatured. The denatured, Cy5-labeled cDNA molecules were then allowed to hybridize with the array on the slides at 67° C. for 12 hours or overnight under standard conditions set forth in the Operon Technologies, Inc. "Hybridization Protocol, Microarrays" (2001) protocol, incorporated herein by reference. Following the hybridization step, the array was washed in 2×SSC, 0.2% SDS for approximately 1 minute, then in 0.2×SSC, and then in 0.05×SSC, following the Operon Technologies, Inc. "Hybridization Protocol, Microarrays" (2001) protocol to remove non-hybridized cDNA. The slide was dried prior to carrying out optical scanning, as described below.

Cy5 is a fluorescent dye having an optical absorption maximum at 649 nm and an emission maximum at 670 nm. To demonstrate that the approach of this invention is just as effective even when the optical labeling molecules are not fluorescent, the Cy5 label on the hybridized cDNA was photo-bleached until no measurable fluorescence could be detected with a standard commercial fluorescence scanner.

For an oblique-incidence reflectivity-difference scan as illustrated in FIG. 1, we use a 5 milli-Watt linearly-polarized He—Ne laser (model LGK7654-7, LASOS, Ebersberg, Germany). The initial polarization, set by passing incident beam (102) through a polarizer (model 5524, New Focus, San Jose, Calif.) (103) is along the s-polarization direction. The incident beam (102) is passed through a photoelastic modulator (104) (model PEM90, Hinds Instruments, Hillsboro, Oreg.) with the two principal axes of the modulator bisecting the initial polarization. Periodically at $\Omega$=50 kHz, the polarization modulator produces an output polarization that is changed in a sequence of the originally s-polarization, left-circular polarization, p-polarization, left-circular polarization, s-polarization, right-circular polarization, p-polarization, right-circular polarization, and finally back to s-polarization. The polarization-modulated beam is then passed through a phase-shifter (105), in this instance, a Pockel cell (model Impact10, Cleveland Crystals, Highland Heights, Ohio) with the principal axes of the cell aligned parallel to s- and p-polarizations. The Pockel cell adds between the s- and p-polarized components a phase lag, $\phi$, that can be changed by applying an electrical voltage. The phase-lagged, polarization-modulated beam is focused by a lens (106) on a region of the slide having no DNA features. The reflected beam (107) is passed through another lens (108) and then through an analyzing polarizer (109) (model 5524, New Focus, San Jose, Calif.) with its transmission axis (TA) set an angle of $\theta_{PL}$ with respect to the s-polarization axis. The resultant beam with the intensity $I_R(t)$ is then detected with a biased silicon photodiode (110) (model-818-BB-40, Newport, Irvine, Calif.). The photo-current, in proportion to $I_R(t)$, is sent to two Lock-in amplifiers (model SR830, Stanford Research Systems, Sunnyvale, Calif.) to detect the first and second harmonics in the photo-current, or equivalently, $I_R(t)$.

We null (i.e., minimize the intensity of) the first harmonic by adjusting the voltage on the Pockel cell (105) and null the second harmonic by adjusting the orientation of the transmission axis of the analyzer (109). To obtain Im$\{\Delta_p-\Delta_s\}$, we measure the factor $c_1(N=1)I_{inc}|r_{p0} \sin \theta_{PL}|^2$ by adjusting the voltage on Pockel cell (105) until the detected first harmonic signal is maximized. We divide the subsequently measured first harmonic signal (i.e., after the initial nulling) by this maximum signal to deduce Im$\{\Delta_p-\Delta_s\}$ directly. To obtain Re$\{\Delta_p-\Delta_s\}$, we measure the factor $c_2(N=2)I_{inc} |r_{p0} \sin \theta_{PL}|^2$ by inserting another polarizing analyzer either right before the optical beam is incident on the slide surface or immediately after the optical beam is reflected off the slide surface with the transmission axis oriented along either the s-polarization or the p-polarization direction, and measure the second harmonic signal. We divide the subsequently measured second harmonic signal (i.e., after the initial nulling) by two times the second harmonic signal (obtained following insertion of the s-polarization or p-polarization oriented analyzer), and then multiply the result by the analyzer transmittance for the passing polarization to deduce Re$\{\Delta_p-\Delta_s\}$.

During the scan, the illuminating optics and detection system were fixed, and the chip was translated by mounting it on top of two orthogonal translation stages (Newport-Klinger, model 462-XY, Irvine, Calif.). 80-pitch screws were attached to each of the stages and the translation stages were moved sequentially by turning the screws with stepper motors. The smallest achievable step size along both the x and y direction on the surface was 0.8 microns in this experiment. To generate the scan shown as FIG. 3(a) through FIG. 3(d), step sizes of 4.8 micron were used for x and y.

Figure 3A:
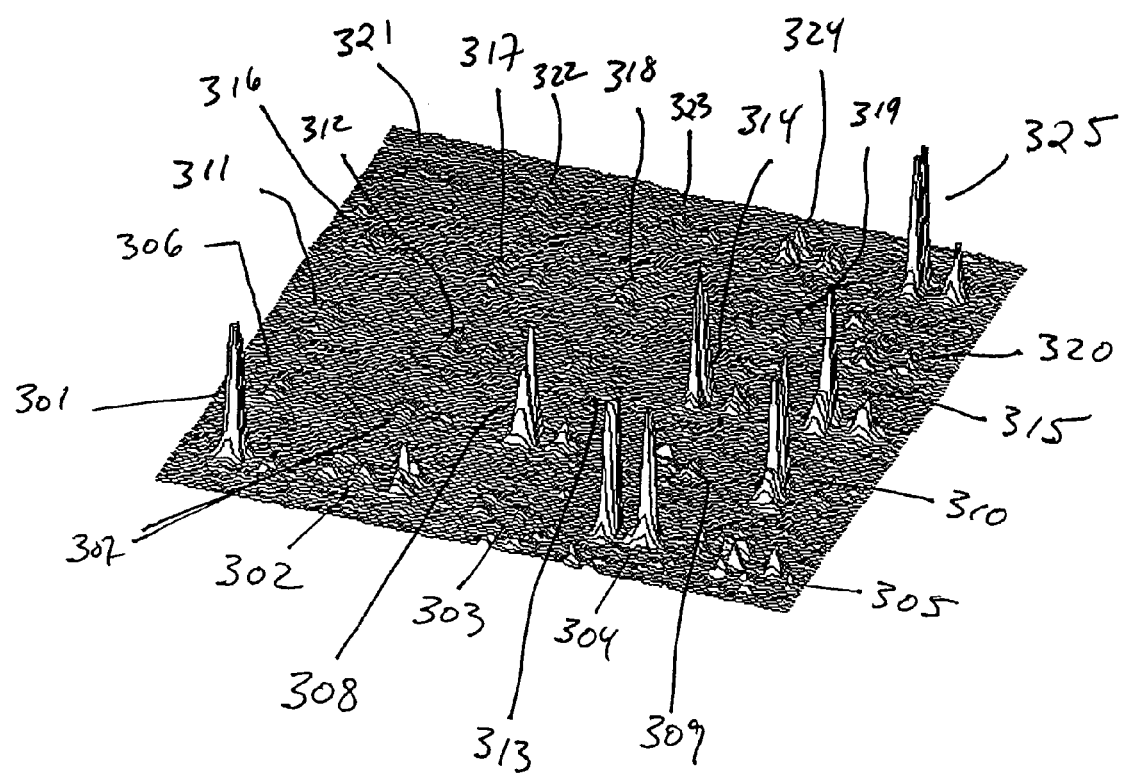
FIGS. 3(a)–3(d) illustrate scans over a region of a microarray containing 5×5 (=25) printed features of 60-mer DNA oligonucleotides hybridized with Cy5-labeled cDNA.

FIG. 3(a) shows a plot of Im$\{\Delta_p-\Delta_s\}$, corresponding to changes in refractive index, over a region that contains a square array of 5×5=25 printed features. 9 of the 25 distinct 60-mer oligos have hybridized with the Cy5-labeled cDNA molecules. Peaks 301, 302, 304, 308, 310, 314, 315, 324, and 325 shown in FIG. 3(a) correspond to hybridized features. Other features with much smaller and yet well distinguished lobes (i.e., peaks 303, 305–307, 309, 311–313, and 316–323) are those features that did not hybridize with the Cy5-labeled cDNA. On average, the peak heights for the hybridized features [Im$\{\Delta p-\Delta s\}$~0.05] are 50 times the peak heights of those features that did not hybridize with the Cy5-labeled cDNA [Im$\{\Delta p-\Delta s\}$~0.001].

Figure 3B:
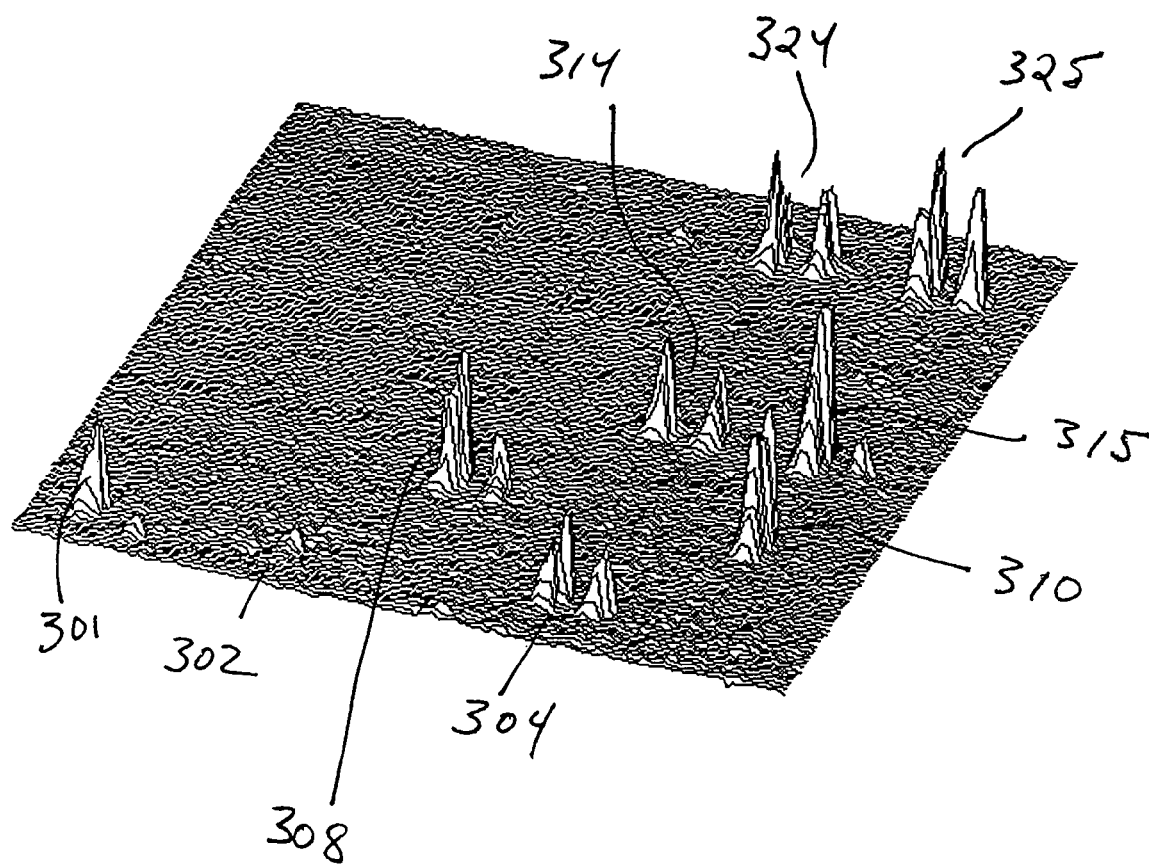

FIG. 3(b) shows a plot of Re$\{\Delta_p-\Delta_s\}$, corresponding to changes in optical absorption coefficient, for the same array region as shown in FIG. 3(a). The changes in optical absorption coefficients arise from the presence of the Cy5 dye in the labeled cDNA. Unlike Im$\{\Delta_p-\Delta_s\}$ (corresponding to refractive index changes, allowing even the unlabeled 60-mers to be imaged), for Re$\{\Delta_p-\Delta_s\}$, only those features where successful hybridization has taken place [i.e., FIG. 3(b) peaks 301, 302, 304, 308, 310, 314, 315, 324 and 325] exhibit prominent peaks corresponding to the same peaks in FIG. 3(a). The maximum value of Re$\{\Delta_p-\Delta_s\}$ is ~0.064

(peak 315). As expected, there are no detectable peaks in Re$\{\Delta_p-\Delta_s\}$ for array features that did not hybridize to the labeled cDNA.

Figure 3C:
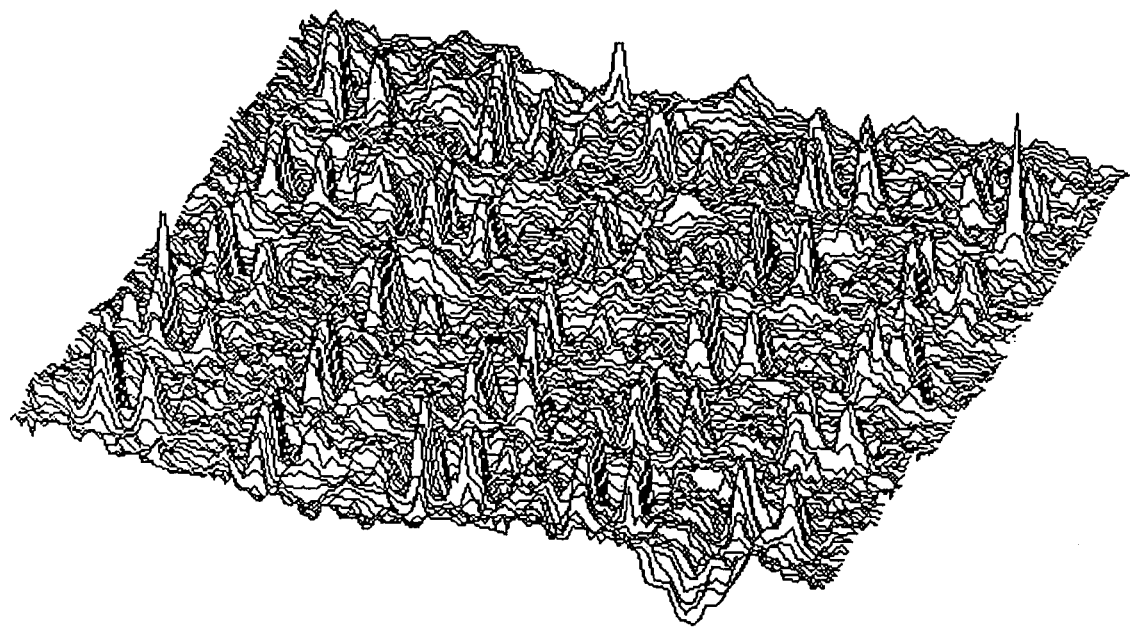

FIG. 3(c) shows a plot of Im$\{\Delta_p-\Delta_s\}$ (corresponding to refractive index changes) for another region of the slide containing a different array of features. This array was printed using a different set of 25 distinct 60-mer oligos whose sequences were designed so as to not be complementary to any of the labeled cDNA sequences. As expected, none of the features in this array hybridized with the sample cDNA molecules. Because the Im$\{\Delta_p-\Delta_s\}$ scan tracks refractive index changes, features corresponding to the unlabeled 60-mer oligos are clearly detected. Each spot yet again consists of two lobes. The average Im$\{\Delta_p-\Delta_s\}$ peak value of the lobes is ~0.001. The scale of FIG. 3(c) is expanded from that of FIG. 3(a) by a factor of 25.

Figure 3D:
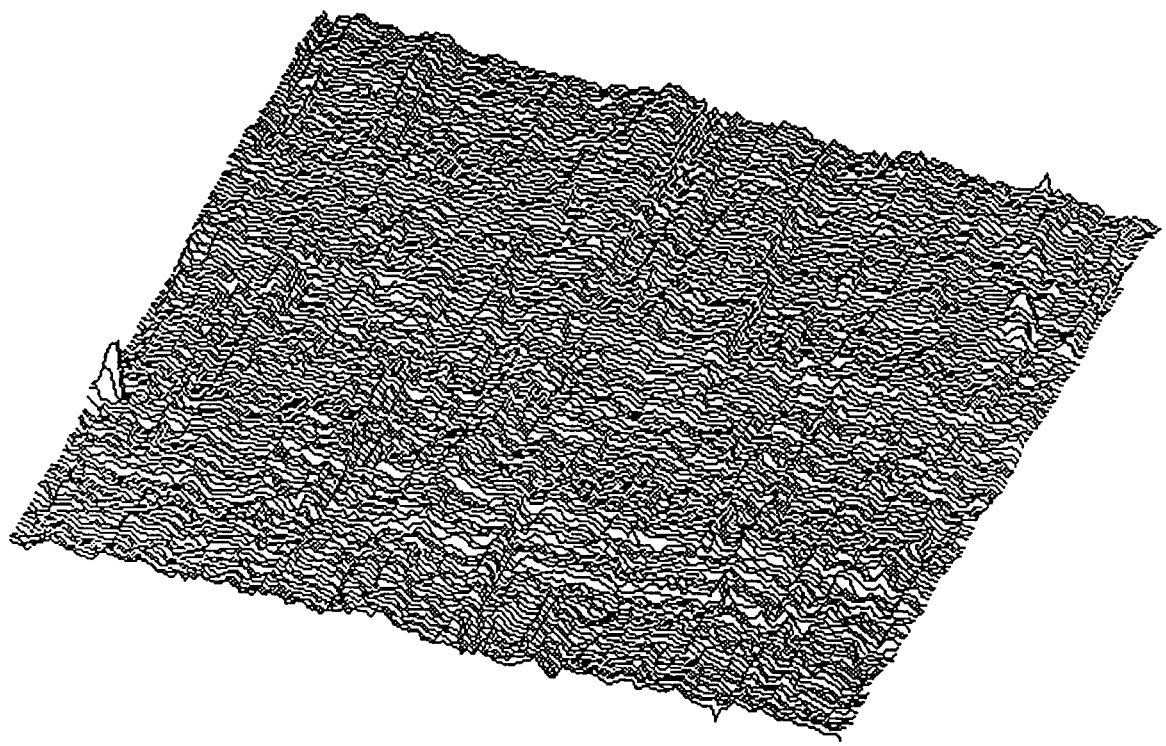

FIG. 3(d) shows a plot of Re$\{\Delta_p-\Delta_s\}$, corresponding to changes in optical absorption coefficient, for the same array region shown in FIG. 3(c). The scale of FIG. 3(d) is expanded from that of FIG. 3(b) by a factor of 6. Because no hybridization took place in this array, we expect no optically absorbing materials to be present in these array features. This is indeed the case, as no discernable features are observable above the background noise [FIG. 3(d)]. In contrast, FIG. 3(c) shows that the molecular densities and the resultant refractive indices inside these features are significantly different from those of the surrounding region. This means that even without labeling agents, the methods of the invention allow monitoring and measurement of density variations of the features on a microarray slide. See Appendix Special Case 4.

The cDNA molecules that hybridized with some of the 60-mer oligos on the array contain photo-bleached Cy5 molecules that are still strongly absorbing at the 633 nm wavelength of our probe laser (near the 647 nm Cy5 absorption peak). The strong absorption gives rise to large changes in the refractive index and optical absorption coefficient within the hybridized features. This is reflected in the 50-fold changes in Im$\{\Delta_p-\Delta_s\}$ from the unhybridized to hybridized features [FIG. 3(a)], and in similar changes in Re$\{\Delta_p-\Delta_s\}$ [FIG. 3(b)]. Note there is no detectable fluorescence yield from these photo-bleached Cy5 molecules.

Since the large changes in the refractive index and optical absorption coefficient are highly wavelength-dependent, one may readily use two optical labeling agents with the absorption maxima peaking at two sufficiently separated wavelengths for two sets of cDNA molecules. In doing so and by scanning the features with two appropriate lasers as is common practice in fluorescence scanners, the difference in the degree of hybridization between the two sets can be determined and quantified without measurement of fluorescence yield and the difficulties attending such measurement.

EXAMPLE 3

Characterization of Xenon Monolayer Growth on Nb (110)

As a model system for heteroepitaxy on a highly mismatched substrate, we studied the vapor-phase epitaxy of Xe on Nb(110) from 33 K to 100 K using a combination of low energy electron diffraction (LEED) and the in-situ oblique-incidence reflectivity difference approach of the invention. We use the same experimental setup as shown in FIG. 1 and the same optical components as described in Example 1 except that the phase-lagged, polarization-modulated beam remains collimated when it illuminates and subsequently reflects off the clean and Xe covered Nb(110) surface.

Figure 4:
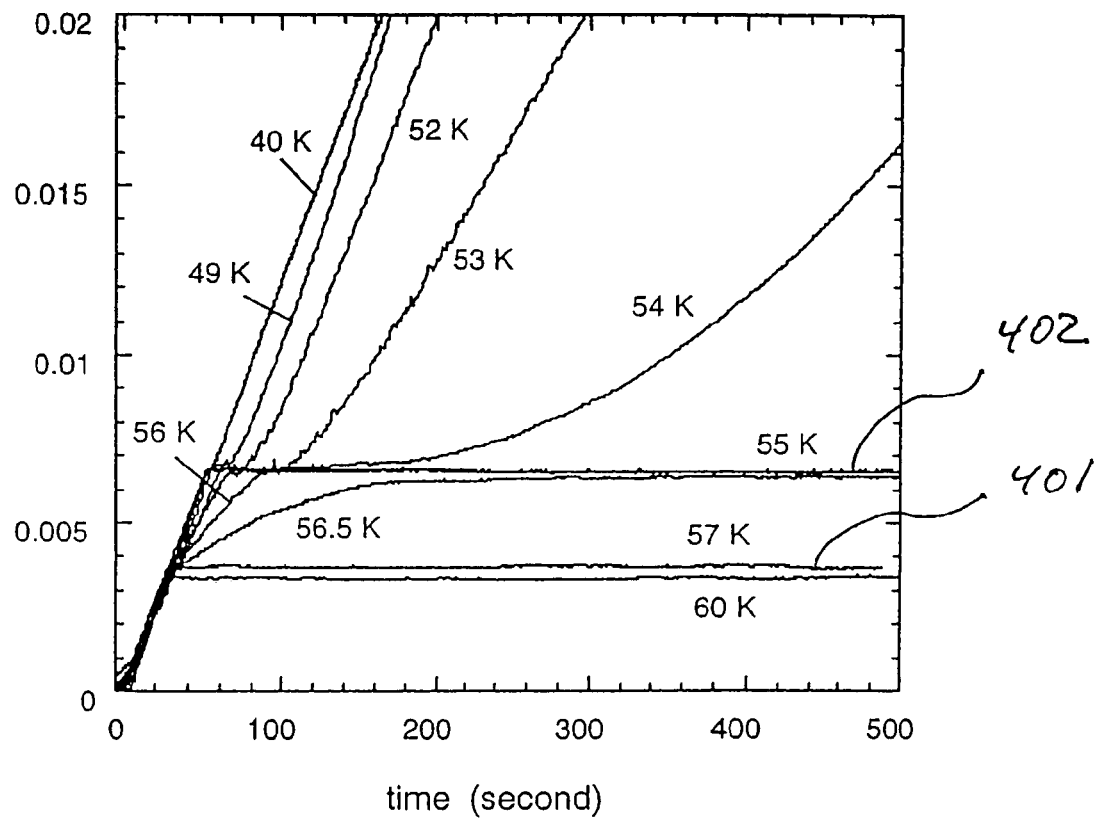
FIG. 4 illustrates $\text{Im}\{\Delta_p - \Delta_s\}$ during continuous growth of xenon monolayers on Nb(110) at different temperatures.

Let $r_{p0}=|r_{p0}|\exp(i\Phi_{p0})$ and $r_{s0}=|r_{s0}|\exp(i\Phi_{s0})$ be the reflection coefficients for p- and s-polarized light at $\lambda=6328$ Å (LGK7654-7 He—Ne laser wavelength) from a clean Nb(110) substrate before deposition of xenon. Let $r_p=|r_p|\exp(i\Phi_p)$ and $r_s=|r_s|\exp(i\Phi_s)$ be the reflection coefficients for p- and s-polarized light coefficients after a Xe layer is deposited on the substrate. As above, we define $\Delta_p=(r_p-r_{p0})/r_{p0}$ and $\Delta_s=(r_s-r_{s0})/r_{s0}$. Before deposition, we null the first harmonic by adjusting the phase lag introduced by the Pockel cell and null the second harmonic by adjusting the orientation of the analyzer transmission axis with respect to the s-polarization axis. Subsequently we expose the clean Nb(110) surface to an ambient of xenon gas at $1.4\times10^{-7}$ Torr. The change in the first harmonic is converted to Im$\{\Delta_p-\Delta_s\}$ by using the same procedure described in Example 2. The change in the second harmonic is converted to Re$\{\Delta_p-\Delta_s\}$ using the same procedure described in Example 2. FIG. 4 shows on the ordinate Im$\{\Delta_p-\Delta_s\}$ (corresponding to refractive index changes) vs. the deposition time (abscissa) during the Xe growth on Nb(110) from 40 K to 60 K. Two plateaus (401, 402) mark completion of first and second monolayers of xenon on Nb(110).

Figure 5:
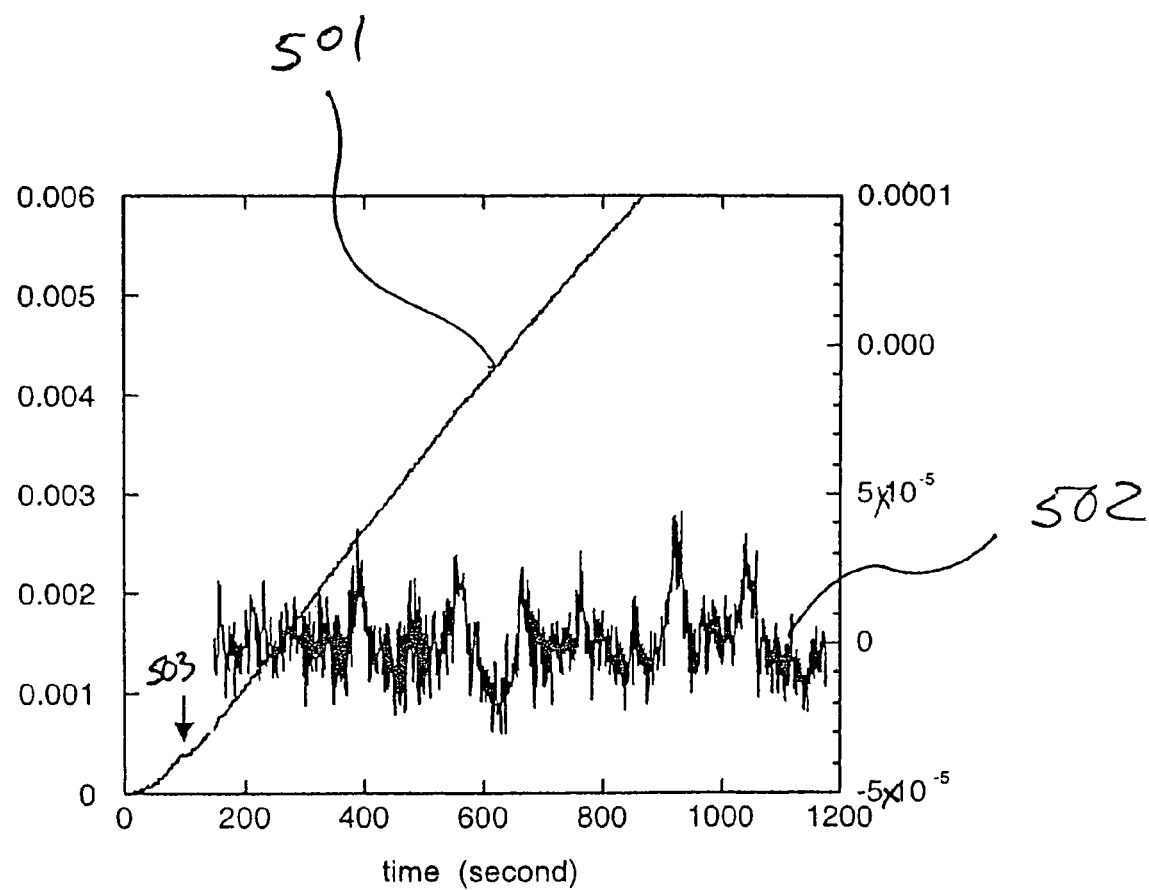
FIG. 5. illustrates $\text{Re}\{\Delta_p - \Delta_s\}$ during continuous growth of xenon monolayers on Nb(110) at 40 K.

FIG. 5 shows on the ordinate Re$\{\Delta_p-\Delta_s\}$ (corresponding to optical absorption coefficient changes) vs. deposition time (abscissa) during the Xe growth on Nb(110) at 40 K. The difference (502) between the original signal (501) and the envelope part of the signal (not shown) reveals peaks that are roughly periodic with the deposition time. The peaks are indicative of an incomplete layer-by-layer growth that is dominated by a step-flow growth at this temperature. Arrowhead 503 marks completion of two monolayers. Left ordinate is Re$\{\Delta_p-\Delta_s\}$, right ordinate is variation in Re$\{\Delta_p-\Delta_s\}$.

EXAMPLE 4

Characterization and Control of Lead (Pb) growth on Cu (100) in Electrochemical Deposition Environment We have studied the electrodeposition of monolayers of lead (Pb) on a Cu(100) surface using the methods of the present invention. This example illustrates application of the methods for characterizing and controlling in situ the growth and removal of a thin film of a third material at the interface between two materials, one of which being a liquid and the other is a solid. In electrodeposition, the growth of the third material at the interface is governed by the chemical make-up of the liquid containing the third material and the electrostatic potential difference between the liquid and the solid material.

Figure 6A:
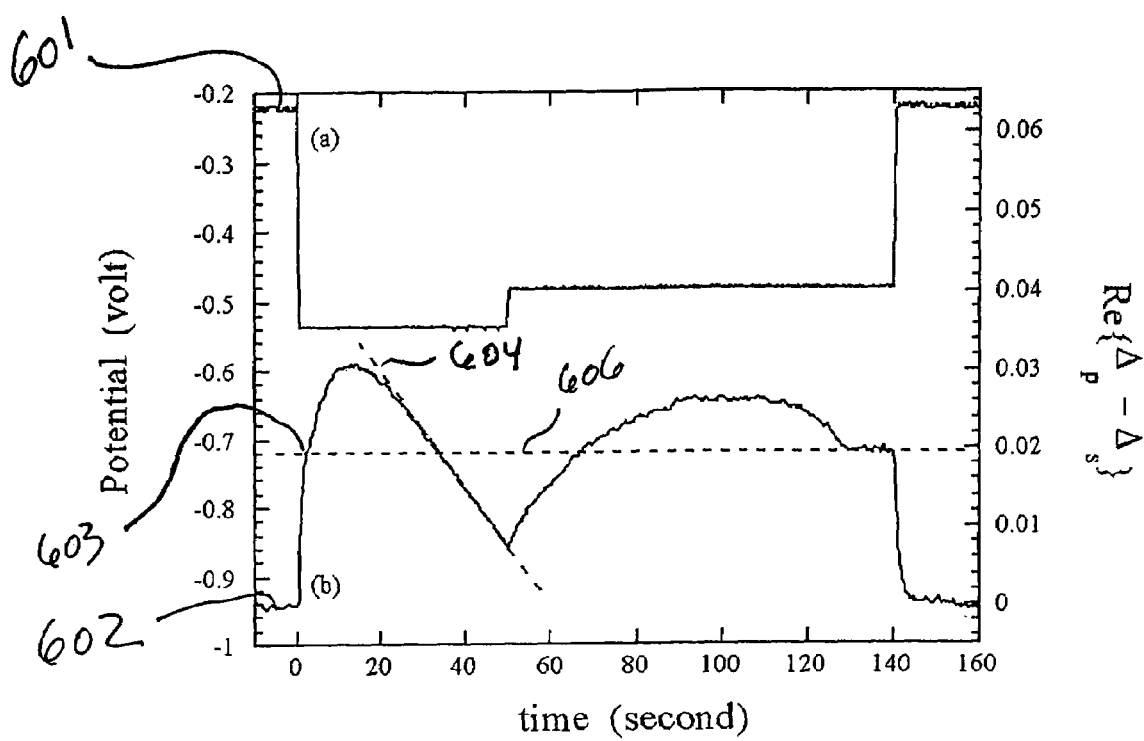
FIGS. 6(a)–6(b) respectively illustrate $\text{Re}\{\Delta_p - \Delta_s\}$ and $\text{Im}\{\Delta_p - \Delta_s\}$ during electrodeposition of Pb monolayers on Cu(100) as a function of applied potential and time.
Figure 6B:
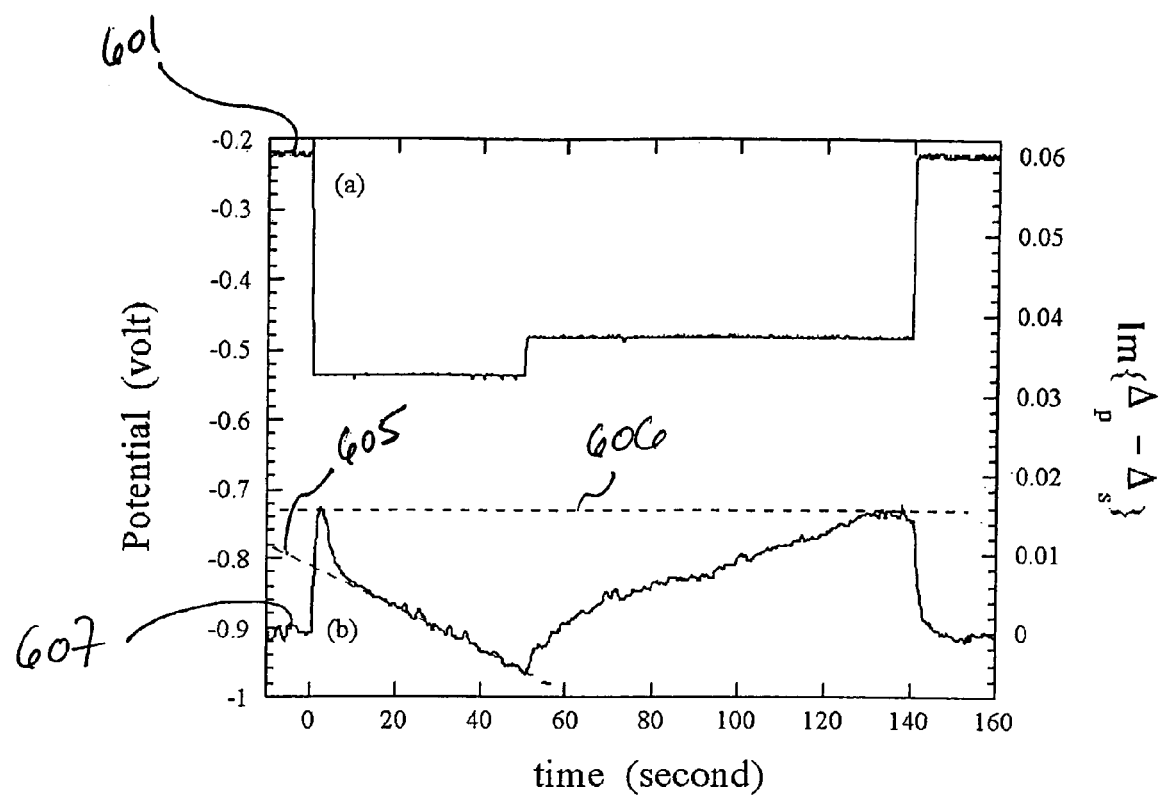

FIG. 6(a) shows Re$\{\Delta_p-\Delta_s\}$ (602) vs. time during Pb growth on Cu(100) at room temperature as the potential is changed in a step-wise manner. FIG. 6(b) shows the corresponding Im$\{\Delta_p-\Delta_s\}$ (607). When the potential (601) is initially stepped down from −0.222 V to −0.535 V, Re$\{\Delta_p-\Delta_s\}$ (602) increases from zero to 0.02 at which point the slope of the increase significantly decreases. This crossover point (603) marks the deposition of the first monolayer of Pb on Cu. The dotted horizontal line (606) marks the signal level in response to the deposition of the first Pb monolayer in the form of an alloy. The magnitude of the increase (~0.02) indicates that the first Pb monolayer forms an alloy with the topmost Cu layer. After roughly 20 seconds when a transition layer is formed on top of the first monolayer, a bulk-like, compact Pb film starts to grow as indicated by a linear decrease in Re$\{\Delta_p-\Delta_s\}$ (604) and Im$\{\Delta_p-\Delta_s\}$ (605). When the potential is stepped back to −0.48 V at which only the first Pb monolayer is stable on Cu(100), the Pb overlayer on top of the first Pb monolayer (in alloy form) starts to dissolve into the liquid. Correspondingly $\text{Re}\{\Delta_p-\Delta_s\}$ and $\text{Im}\{\Delta_p-\Delta_s\}$ change in a backward manner almost along their original paths until the values corresponding to the first monolayer are reached. When the potential is increased again from −0.48 V to −0.222 V, the first Pb monolayer in form of alloy also dissolves in the solution and the Cu(100) is essentially restored. The quantitative difference in optical signals for growth and dissolution are due to the irreversibility in the film morphology evolution as different kinetics are predominant during growth and dissolution.

As FIGS. 6(a) and (b) illustrate, the thickness and morphology of the thin film of said third material or the electrodeposition process in general can be controlled in situ by controlling the potential as a function of time using the optical signals generated by the methods of the invention as feedback parameters.

Appendix

Let $r_{p0}=|r_{p0}|\exp(i\Phi_{p0})$ and $r_{s0}=|r_{s0}|\exp(i\Phi_{s0})$ respectively be the reflection coefficients for p- and s-polarized light from a surface. Let the optical dielectric constant of the material on the incidence side be $\epsilon_{inc}\equiv(n_{inc}+i\kappa_{inc})^2$, with $n_{inc}$ and $\kappa_{inc}$ being the corresponding refractive index and optical absorption coefficient. Let the optical dielectric constant of the material on the transmission side be $\epsilon_s=(n_s+i\kappa_s)^2$, with $n_s$ and $\kappa_s$ being the corresponding refractive index and optical absorption coefficient. Let $r_p=|r_p|\exp(i\Phi_p)$ and $r_s=|r_s|\exp(i\Phi_s)$ respectively be the reflection coefficients for p- and s-polarized light from said surface when it is covered with a thin layer of a third material with refractive index $n_d$ and optical absorption coefficient $\kappa_d$. The optical dielectric constant of said third material of interest is $\epsilon_d=(n_d+i\kappa_d)^2$. The thickness of said third material is d. Let $\Delta_p=(r_p-r_{p0})/r_{p0}$ and $\Delta_s=(r_s-r_{s0})/r_{s0}$. It can be shown that:

$$\Delta_p - \Delta_s = -i\left(\frac{4\pi\cos\theta_{inc}\sin^2\theta_{inc}d}{\lambda}\right)\frac{\sqrt{\epsilon_{inc}}\,\epsilon_s(\epsilon_d-\epsilon_{inc})(\epsilon_d-\epsilon_s)}{\epsilon_d(\epsilon_s^2\cos^2\theta_{inc}-\epsilon_{inc}\epsilon_s+\epsilon_{inc}^2\sin^2\theta_{inc})} \quad (3)$$

where $\lambda$ is the wavelength of the light beam in vacuo. $\theta_{inc}$ is the angle of incidence.

General Case: Absorptive Materials on Both Sides of a Thin Layer of a Third Material (i.e., $\text{Im}\{\epsilon_s\}\neq 0$, $\text{Im}\{\epsilon_{inc}\}\neq 0$)

We measure both $\text{Re}\{\Delta_p-\Delta_s\}$ and $\text{Im}\{\Delta_p-\Delta_s\}$. Knowing $\epsilon_s$ and $\epsilon_{inc}$, we solve for $\epsilon_d$ as follows $$\epsilon_d = \frac{(\epsilon_s+\epsilon_{inc}-A)\pm\sqrt{(\epsilon_s+\epsilon_{inc}-A)^2-4\epsilon_s}}{2} \quad (4)$$

Here we have defined $$A = i\frac{(\Delta_p-\Delta_s)\lambda(\epsilon_s^2\cos^2\theta_{inc}-\epsilon_{inc}\epsilon_s+\epsilon_{inc}^2\sin^2\theta_{inc})}{4\pi\cos\theta_{inc}\sin^2\theta_{inc}\epsilon_s\sqrt{\epsilon_{inc}}\,d} \quad (5)$$

Special Case 1: Transparent Materials on Both Sides of a Thin Layer of a Third Material (i.e., $\text{Im}\{\epsilon_s\}=\text{Im}\{\epsilon_{inc}\}=0$)

From Equation (3), one can see that $\text{Re}\{\Delta_p-\Delta_s\}$ is non-vanishing only if said third material is absorptive, $\kappa_d\neq 0$. Consequently $\text{Re}\{\Delta_p-\Delta_s\}$ corresponds primarily to the optical absorption coefficient of said third material. When $\kappa_d=0$, $\text{Re}\{\Delta_p-\Delta_s\}$ vanishes. In this case non-vanishing $\text{Im}\{\Delta_p-\Delta_s\}$ corresponds to the difference in the refractive indices of the third material and the materials on both sides of the thin layer.

Special Case 2: Transparent Materials on Both Sides of a Thin Layer of a Third Material (i.e., $\text{Im}\{\epsilon_s\}=\text{Im}\{\epsilon_{inc}\}=0$), $\epsilon_d$ Deviates Slightly from $\epsilon_s$ In this case, Equation (3) can be simplified as $$\Delta_p - \Delta_s = -i\left[\frac{4\pi d\cos\theta_{inc}\sin^2\theta_{inc}\sqrt{\epsilon_{inc}}}{\lambda(\epsilon_s\cos^2\theta_{inc}-\epsilon_{inc}\sin^2\theta_{inc})}\right](\epsilon_d-\epsilon_s). \quad (6)$$

Let the refractive index difference be $\delta n_d=n_d-n_s$, we can rewrite Equation (6) as $$\Delta_p - \Delta_s = \left[\frac{8\pi d\cos\theta_{inc}\sin^2\theta_{inc}\sqrt{\epsilon_{inc}}\,n_s}{\lambda(\epsilon_s\cos^2\theta_{inc}-\epsilon_{inc}\sin^2\theta_{inc})}\right](\kappa_d-i\delta n_d). \quad (7)$$

From Equation (7), one finds that $\text{Re}\{\Delta_p-\Delta_s\}$ measures the optical absorption coefficient of a third material while $\text{Im}\{\Delta_p-\Delta_s\}$ measures the difference in the refractive indices of the third material and the material on the transmission side.

Special Case 3: Transparent Materials on Both Sides (i.e., $\text{Im}\{\epsilon_s\}=\text{Im}\{\epsilon_{inc}\}=0$), $\epsilon_d$ Deviates Slightly from $\epsilon_{inc}$ In this case, Equation (3) can be simplified as $$\Delta_p - \Delta_s = +i\left[\frac{4\pi d\cos\theta_{inc}\sin^2\theta_{inc}\epsilon_s}{\lambda\sqrt{\epsilon_{inc}}\,(\epsilon_s\cos^2\theta_{inc}-\epsilon_{inc}\sin^2\theta_{inc})}\right](\epsilon_d-\epsilon_{inc}) \quad (8)$$

Let the refractive index difference be $\delta n_d=n_d-n_{inc}$, we can rewrite Equation (8) as $$\Delta_p - \Delta_s = \left[\frac{8\pi d\cos\theta_{inc}\sin^2\theta_{inc}\epsilon_s}{\lambda(\epsilon_s\cos^2\theta_{inc}-\epsilon_{inc}\sin^2\theta_{inc})}\right](-\kappa_d+i\delta n_d) \quad (9)$$

From Equation (9), one finds that $\text{Re}\{\Delta_p-\Delta_s\}$ measures the optical absorption coefficient of the third material while $\text{Im}\{\Delta_p-\Delta_s\}$ measures the difference in the refractive indices of said third material and the material on the incidence side.

Special Case 4: Transparent Materials on Both Sides (i.e., $\text{Im}\{\epsilon_s\}=\text{Im}\{\epsilon_{inc}\}=0$), $\epsilon_d$ Deviates Slightly from $\epsilon_{inc}=1$, and a Thin Layer of a Third Material that Consists of Molecules In this case, $$\epsilon_d - 1 \cong 4\pi\gamma_{mol}N_s(x,y;t)/d \quad (10)$$

where $\gamma_{mol}$ is the molecular polarizability of said third material, $N_s(x,y;t)$ is the surface density of the molecules that may vary as functions of spatial coordinates (x and y) along the interface and/or as a function of time (t), d is the thickness of the thin layer. Consequently Equation (8) can be simplified as $$\Delta_p - \Delta_s = +i\left[\frac{16\pi^2\cos\theta_{inc}\sin^2\theta_{inc}\varepsilon_s\gamma_{\text{mol}}}{\lambda(\varepsilon_s\cos^2\theta_{inc} - \sin^2\theta_{inc})}\right]N_s(x, y; t) \quad (11)$$

From Equation (11), one can measure the surface density differences as results of displacements in spatial coordinates and/or in time from the measurements of $\text{Im}\{\Delta_p-\Delta_s\}$ and $\text{Re}\{\Delta_p-\Delta_s\}$, independent of the thickness of the layer. In cases when the molecular polarizability $\gamma_{mol}$ is known or can be ascertained, one can determine the surface density $N_s(x, y;t)$ quantitatively from $\text{Im}\{\Delta_p-\Delta_s\}$ and $\text{Re}\{\Delta_p-\Delta_s\}$ using Eq. (11).

The invention claimed is:

1. An optical device, comprising:
   a sample holder;
   a light source for emitting a polarized incident light beam, said polarized incident light beam forming an incidence angle with a sample held by said sample holder;
   a polarization modulator that modulates at a modulation frequency the polarization of at least one of said incident light beam or a light beam reflected off a sample held by said sample holder;
   an adjustable phase shifter located within said incident light beam path or said reflected light beam path;
   a detector located within said reflected light beam path, wherein said detector is capable of transducing said reflected light beam intensity to a variable electrical signal; and
   a signal analyzer for receiving said variable electrical signal from said detector and determining a magnitude of a frequency component corresponding to a harmonic frequency of said modulation frequency.

2. The device of claim 1, wherein said incidence angle is oblique.

3. The device of claim 2, wherein said polarization modulator is selected from the group consisting of a photoelastic modulator, an electro-optic phase modulator, a rotatable wave plate, a rotatable double-Fresnel rhomb, a rotatable reflecting surface, and a pair of rotatable reflecting surfaces.

4. The device of claim 2, wherein said adjustable phase shifter is selected from the group consisting of a voltage-controlled Pockel cell, a mechanically controlled Soleil-Babinet compensator, a Berek compensator, and a double-Fresnel rhomb achromatic retarder.

5. The device of claim 2, wherein said adjustable phase shifter is located within said incident light beam path.

6. The device of claim 2, wherein said adjustable phase shifter is located within said reflected light beam path.

7. The device of claim 2, further comprising a polarizer or an analyzer located within said reflected light beam path between said sample holder and said detector.

8. The device of claim 7, comprising said polarizer.

9. The device of claim 7, comprising said analyzer.

10. The device of claim 1, wherein said incidence angle is near-normal.

11. The device of claim 10, wherein said polarization modulator is selected from the group consisting of a photoelastic modulator, an electro-optic phase modulator, a rotatable wave plate, a rotatable double-Fresnel rhomb, a rotatable reflecting surface, and a pair of rotatable reflecting surfaces.

12. The device of claim 10, wherein said adjustable phase shifter is selected from the group consisting of a Faraday rotator, and a material capable of adding a relative phase difference to the R and the L components of a circularly-polarized light beam.

13. The device of claim 10, wherein said adjustable phase shifter is located within said incident light beam path.

14. The device of claim 10, wherein said adjustable phase shifter is located within said reflected light beam path.

15. The device of claim 10, further comprising a wave plate and a polarizer or a wave plate and an analyzer located within said reflected light beam path between said sample holder and said detector.

16. The device of claim 15, comprising said wave plate and said polarizer.

17. The device of claim 15, comprising said wave plate and said analyzer.

18. An optical device, comprising:
   a sample holder;
   a light source for emitting a polarized incident light beam, said polarized incident light beam forming an incidence angle with a sample held by said sample holder;
   a polarization modulator that modulates at a modulation frequency the polarization of at least one of said incident light beam or a light beam reflected off a sample held by said sample holder;
   an analyzer or a combination of a wave plate and an analyzer located within said incident light beam path or said reflected light beam path, wherein the orientation of said analyzer transmission axis, $\theta_{PL}$, is adjustable;
   a detector located within said reflected light beam path, wherein said detector is capable of transducing said reflected light beam intensity to a variable electrical signal; and
   a signal analyzer for receiving said variable electrical signal from said detector and determining a magnitude of a frequency component corresponding to a harmonic frequency of said modulation frequency.

19. The device of claim 18, wherein said incidence angle is oblique.

20. The device of claim 19, wherein said polarization modulator is selected from the group consisting of a photoelastic modulator, an electro-optic phase modulator, a rotatable wave plate, a rotatable double-Fresnel rhomb, a rotatable reflecting surface, and a pair of rotatable reflecting surfaces.

21. The device of claim 19, further comprising a polarizer located within said reflected light beam path between said sample holder and said detector.

22. The device of claim 18, wherein said incidence angle is near-normal.

23. The device of claim 22, wherein said polarization modulator is selected from the group consisting of a photoelastic modulator, an electro-optic phase modulator, a rotatable wave plate, a rotatable double-Fresnel rhomb, a rotatable reflecting surface, and a pair of rotatable reflecting surfaces.

24. The device of claim 22, wherein said wave plate and said analyzer are located within said incident light beam path, and further comprising a second wave plate and a polarizer located within said reflected light beam path between said sample holder and said detector.

25. An optical device, comprising:
   a sample holder;
   a light source for emitting a polarized incident light beam, said polarized incident light beam forming a near-normal incidence angle with a sample held by said sample holder;

a material within said incident light beam path capable of adding a relative magnitude difference to the R and the L components of said polarized incident light beam;

a polarization modulator that modulates at a modulation frequency the polarization of a light beam reflected off a sample held by said sample holder;

a wave plate and a polarizer located within said reflected light beam path, wherein the orientation of said polarizer transmission axis, $\theta_{PL}$, is adjustable;

a detector located within said reflected light beam path, wherein said detector is capable of transducing said reflected light beam intensity to a variable electrical signal; and a signal analyzer for receiving said variable electrical signal from said detector and determining a magnitude of a frequency component corresponding to a harmonic frequency of said modulation frequency.

* * * * *